United States Patent
Hamilton et al.

(10) Patent No.: US 7,700,638 B2
(45) Date of Patent: Apr. 20, 2010

(54) 1,5,7-TRISUBSTITUTED BENZIMIDAZOLE DERIVATIVES AND THEIR USE FOR MODULATING THE GABA$_A$ RECEPTOR COMPLEX

(75) Inventors: Niall Morton Hamilton, Glasgow (GB); Susan Elizabeth Napier, Lanarkshire (GB); Morag Ann MacCall Easson, Edinburgh (GB); Andrew John Cooke, East Kilbride (GB); Lene Teuber, Værløse (DK); Naheed Mirza, Birkerød (DK); Frank Wätjen, Farum (DK)

(73) Assignees: N. V. Organon, AB Oss (NL); Neurosearch A/S, Ballerup (DK)

( * ) Notice: Subject to any disclaimer, the term of this patent is extended or adjusted under 35 U.S.C. 154(b) by 756 days.

(21) Appl. No.: 10/575,380

(22) PCT Filed: Oct. 20, 2004

(86) PCT No.: PCT/EP2004/052582

§ 371 (c)(1),
(2), (4) Date: Apr. 11, 2006

(87) PCT Pub. No.: WO2005/040131

PCT Pub. Date: May 6, 2005

(65) Prior Publication Data

US 2007/0021482 A1    Jan. 25, 2007

Related U.S. Application Data

(60) Provisional application No. 60/513,609, filed on Oct. 24, 2003.

(30) Foreign Application Priority Data

Oct. 23, 2003    (DK) ............................. 2003 01566

(51) Int. Cl.
*A61K 31/4184* (2006.01)
*C07D 235/04* (2006.01)

(52) U.S. Cl. ................. 514/394; 548/302.7; 548/304.4; 548/310.4; 514/385; 514/393

(58) Field of Classification Search ............. 548/302.7, 548/304.4, 310.4; 514/385, 393, 394
See application file for complete search history.

(56) References Cited

U.S. PATENT DOCUMENTS 5,554,630 A * 9/1996 Teuber et al. ............... 514/338
5,554,632 A * 9/1996 Teuber et al. ............... 514/338

FOREIGN PATENT DOCUMENTS

EP    0 616 807 A1    9/1994
WO    WO-00/78728 A1    12/2000

* cited by examiner

*Primary Examiner*—Golam M Shameem
(74) *Attorney, Agent, or Firm*—Birch, Stewart, Kolasch & Birch, LLP

(57) ABSTRACT

This invention relates to novel 1,5,7-trisubstituted benzimidazole derivatives, pharmaceutical compositions containing these compounds, and methods of treatment therewith.

The compounds of the invention are useful in the treatment of central nervous system diseases and disorders, which are responsive to modulation of the GABA$_A$ receptor complex.

8 Claims, No Drawings

1,5,7-TRISUBSTITUTED BENZIMIDAZOLE DERIVATIVES AND THEIR USE FOR MODULATING THE GABA$_A$ RECEPTOR COMPLEX

This National Phase application claims priority under 35 U.S.C. 119(e) to U.S. Provisional Application No. 60/513,609 filed on Oct. 24, 2003 and under 35 U.S.C. 119(a) to Patent Application No. PA 2003 01566 filed in Denmark on Oct. 23, 2003. Both of these prior applications are hereby expressly incorporated by reference into the present application.

TECHNICAL FIELD

This invention relates to novel 1,5,7-trisubstituted benzimidazole derivatives pharmaceutical compositions containing these compounds, and methods of treatment therewith.

The compounds of the invention are useful in the treatment of central nervous system diseases and disorders, which are responsive to modulation of the GABA$_A$ receptor complex, and in particular for combating anxiety and related diseases.

BACKGROUND ART

The modulatory sites on the GABA$_A$ receptor complex, such as for example the benzodiazepine receptor, are the target for anxiolytic drugs, such as the classical anxiolytic benzodiazepines. Multiple isoforms of the GABA$_A$ receptor exist; each receptor is a pentameric complex comprising subunits drawn from $\alpha_{1-6}$, $\beta_{1-3}$, $\gamma_{1-3}$, $\delta$, $\epsilon$, and $\theta$ subunit isoforms.

EP 616807 describes benzimidazole compounds for use as benzodiazepine receptor ligands. Furthermore, the five compounds 7-(3-Aminophenyl)-1-phenyl-5-trifluoromethylbenzimidazole, 7-(3-Pyridyl)-1-phenyl-5-trifluoromethylbenzimidazole, 1,7-Diphenyl-5-trifluoromethylbenzimidazole, 7-benzoylamino-1-phenyl-5-trifluoro-methylbenzimidazole, and 7-amino-1-phenyl-5-trifluoromethylbenzimidazole are disclosed therein as intermediates. No pharmaceutical use of these compounds are disclosed.

WO 96/33194, WO 96/33191 and WO 96/33192 describe benzimidazole compounds having affinity for the GABA receptor complex.

WO 98/34923 describes phenylbenzimidazole derivatives as ligands for the GABA receptor complex.

WO 98/17651 and WO 00/78728 describe benzimidazole compounds for use as e.g. anaesthetics.

However, there is a continued strong need to find compounds with an optimised biochemical profile. Furthermore, there is a strong need to find effective compounds without unwanted side effects.

SUMMARY OF THE INVENTION

In its first aspect, the present invention provides compound of formula I:

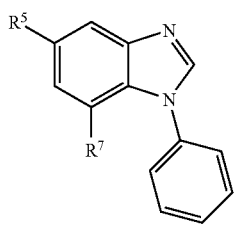

(I)

or an N-oxide thereof, or any of its isomers or any mixture of its isomers, or a pharmaceutically acceptable salt thereof, wherein R$^5$ and R$^7$ are as defined below.

In its second aspect, the invention provides a pharmaceutical composition, comprising a therapeutically effective amount of a compound of the invention, or an N-oxide thereof, or any of its isomers or any mixture of its isomers, or a pharmaceutically acceptable salt thereof, together with at least one pharmaceutically acceptable carrier, excipient or diluent.

In a further aspect, the invention provides the use of a compound of the invention, or an N-oxide thereof, or any of its isomers or any mixture of its isomers, or a pharmaceutically acceptable salt thereof, for the manufacture of a pharmaceutical composition for the treatment, prevention or alleviation of a disease or a disorder or a condition of a mammal, including a human, which disease, disorder or condition is responsive to modulation of the GABA$_A$ receptor complex in the central nervous system.

In a still further aspect, the invention relates to a method for treatment, prevention or alleviation of a disease or a disorder or a condition of a living animal body, including a human, which disorder, disease or condition is responsive to modulation of the GABA$_A$ receptor complex in the central nervous system, which method comprises the step of administering to such a living animal body in need thereof a therapeutically effective amount of a compound of the invention, or an N-oxide thereof, or any of its isomers or any mixture of its isomers, or a pharmaceutically acceptable salt thereof.

Other objects of the invention will be apparent to the person skilled in the art from the following detailed description and examples.

DETAILED DISCLOSURE OF THE INVENTION

1,5,7-trisubstituted Benzimidazole Derivatives

In its first aspect the present invention provides compound of formula I:

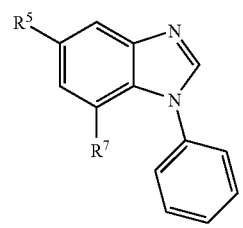

(I)

or an N-oxide thereof, or any of its isomers or any mixture of its isomers, or a pharmaceutically acceptable salt thereof, wherein R$^5$ is halo, trifluoromethyl, trifluoromethoxy, cyano, nitro, alkyl, alkoxy, -alkyl-OR$^a$, —CH=N—O—R$^a$ or —(C=O)—O-alkyl;

wherein R$^a$ is hydrogen or alkyl;

R$^7$ is

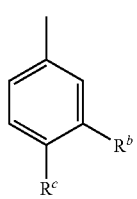

wherein one of R$^b$ and R$^c$ is hydrogen; and the other of R$^b$ and R$^c$ is hydrogen, halo, cyano, hydroxy, nitro, trifluoromethyl, trifluoromethoxy, alkyl, alkoxy, alkylcarbonyl or —NR$^d$—(C=O)—R$^e$;

wherein the alkyl and alkoxy are optionally substituted with one or more substituents selected from the group consisting of: hydroxy, alkoxy, halo, and —NR'R";

$R^d$ and $R^e$ independently of each other are selected from hydrogen and alkyl;

R' and R" independently of each other are selected from hydrogen and alkyl;

—$NR^fR^g$, -alkyl-$NR^fR^g$, —(C=O)—$NR^fR^g$, —O-alkyl-$NR^fR^g$; —$NR_h$-alkyl-$NR^fR^g$;

wherein $R^h$ is hydrogen or alkyl;

$R^f$ and $R^g$ independently of each other are hydrogen or alkyl; or $R^f$ and $R^g$ together with the nitrogen to which they are attached form a 5- to 7-membered heterocyclic ring, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxyalkyl, or —NR'R";

wherein R' and R" independently of each other are hydrogen or alkyl;

or $R^b$ and $R^c$ together represent —O—$CH_2$—O—;

or $R^7$ is

—$NR^h$—(C=O)—$R^i$, —N=CH—$R^i$, or —C≡C—$R^i$;

wherein $R^h$ is hydrogen or alkyl; and $R^i$ is alkyl or phenyl, which alkyl or phenyl is optionally substituted with hydroxy, trifluoromethyl, cyano or alkyl; or —$NR^jR^k$, -alkyl-$NR^jR^k$, —CH=CH—(C=O)—$NR^jR^k$, —CH=CH—(C=O)—O-alkyl, -alkyl-(C=O)—$NR^jR^k$, or —C≡C—$CH^2NR^jR^k$;

wherein $R^j$ and $R^k$ independently of each other are selected from the group consisting of hydrogen, alkyl, -alkyl-CN, -alkyl-R'R" and -alkyl-$R^i$;

wherein R' and R" independently of each other are hydrogen or alkyl;

$R^i$ is a 5- to 7-membered heterocyclic ring comprising one nitrogen atom, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxyalkyl, or —NR'R";

wherein R' and R" independently of each other are hydrogen or alkyl;

or $R^j$ and $R^k$ together with the nitrogen to which they are attached form a 5- to 7-membered heterocyclic ring, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxy, hydroxyalkyl, or —NR'R";

wherein R' and R" independently of each other are hydrogen or alkyl;

or $R^7$ is a heteroaryl group which heteroaryl group is optionally substituted with one or more substituents independently selected from the group consisting of:

halo, trifluoromethyl, trifluoromethoxy, cyano, nitro, alkyl, or alkoxy;

with the proviso that the compound is not 7-(3-Aminophenyl)-1-phenyl-5-trifluoromethylbenzimidazole, 7-(3-Pyridyl)-1-phenyl-5-trifluoromethylbenzimidazole, 1,7-Diphenyl-5-trifluoromethylbenzimidazole, 7-benzoylamino-1-phenyl-5-trifluoromethylbenzimidazole, or 7-amino-1-phenyl-5-trifluoromethylbenzimidazole.

In one embodiment, $R^5$ is halo. In a further embodiment, $R^5$ is trifluoromethyl. In a still further embodiment, $R^5$ is trifluoromethoxy. In a further embodiment, $R^5$ is cyano. In a still further embodiment, $R^5$ is nitro. In a further embodiment, $R^5$ is alkyl such as methyl, ethyl or tertbutyl. In a still further embodiment, $R^5$ is alkoxy. In a further embodiment, $R^5$ is -alkyl-$OR^a$. In a still further embodiment, $R^5$ is —CH=N—O—$R^a$, such as —CH=N—OH or —CH=N—O—$CH_3$. In a further embodiment, $R^5$ is —(C=O)—O-alkyl, such as ethoxycarbonyl. In a still further embodiment, $R^a$ is hydrogen. In a further embodiment, $R^a$ is alkyl. In a further embodiment, $R^5$ is hydroxyalkyl, such as hydroxymethyl.

In a special embodiment, $R^5$ is selected from the group of methyl, tertbutyl, trifluoromethyl, hydroxymethyl, cyano, ethoxycarbonyl, —CH=N—OH and —CH=N—O—$CH_3$.

In a further embodiment, $R^7$ is wherein one of $R^b$ and $R^c$ is hydrogen; and the other of $R^b$ and $R^c$ is hydrogen, halo, cyano, hydroxy, nitro, trifluoromethyl, trifluoromethoxy, alkyl, alkoxy, alkylcarbonyl or —$NR^d$—(C=O)—$R^e$;

wherein the alkyl and alkoxy are optionally substituted with one or more substituents selected from the group consisting of: hydroxy, alkoxy, halo, and —NR'R";

$R^d$ and $R^e$ independently of each other are selected from hydrogen and alkyl;

R' and R" independently of each other are selected from hydrogen and alkyl;

—$NR^fR^g$, -alkyl-$NR^fR^g$, —(C=O)—$NR^fR^g$, —O—$NR^f$$R^g$; —O-alkyl-$NR^fR^g$; —$NR^h$-alkyl-$NR^fR_g$;

wherein $R^h$ is hydrogen or alkyl;

$R^f$ and $R^g$ independently of each other are hydrogen or alkyl; or $R^f$ and $R^g$ together with the nitrogen to which they are attached form a 5- to 7-membered heterocyclic ring, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxyalkyl, or —NR'R";

wherein R' and R" independently of each other are hydrogen or alkyl.

In a further embodiment, $R^b$ is hydrogen. In a still further embodiment, $R^c$ is hydrogen.

In a further special embodiment, the other of $R^b$ and $R^c$ is hydrogen, halo, cyano, hydroxy, nitro, trifluoromethyl, trifluoromethoxy, alkyl, alkoxy, alkylcarbonyl or —NR$^d$—(C=O)—R$^e$; wherein the alkyl and alkoxy are optionally substituted with one or more substituents selected from the group consisting of: hydroxy, halo, and —NR'R"; and R$^d$, R$^e$, R' and R" are as defined above.

In a still further embodiment, the other of R$^b$ and R$^c$ is hydrogen. In a further embodiment, the other of R$^b$ and R$^c$ is halo, such as chloro or fluoro. In a still further embodiment, the other of R$^b$ and R$^c$ is cyano. In a further embodiment, the other of R$^b$ and R$^c$ is hydroxy. In a still further embodiment, the other of R$^b$ and R$^c$ is nitro. In a further embodiment, the other of R$^b$ and R$^c$ is trifluoromethyl. In a still further embodiment, the other of R$^b$ and R$^c$ is trifluoromethoxy. In a further embodiment, the other of R$^b$ and R$^c$ is optionally substituted alkyl, such as alkyl, hydroxyalkyl or haloalkyl. In a special embodiment, the other of R$^b$ and R$^c$ is hydroxymethyl, 1-hydroxyethyl or 2-hydroxy-2-propyl. In a further embodiment, the other of R$^b$ and R$^c$ is alkoxy, such as methoxy. In a still further embodiment, the other of R$^b$ and R$^c$ is alkyl or alkoxy substituted with —NR'R". In a special embodiment, the other of R$^b$ and R$^c$ is aminomethyl, dimethylaminomethyl, diethylaminomethyl or dimethylaminoethoxy. In a further embodiment, the other of R$^b$ and R$^c$ is alkylcarbonyl, such as acetyl. In a further embodiment, the other of R$^b$ and R$^c$ is —NR$^d$—(C=O)—R$^e$, such as acetamido or N-methyl-acetamido. In a still further embodiment, R$^d$ is hydrogen. In a further embodiment, R$^d$ is alkyl, such as methyl. In a still further embodiment, R$^e$ is alkyl, such as methyl.

In a still further embodiment, the other of R$^b$ and R$^c$ is —NR$^f$R$^g$. In a further embodiment, the other of R$^b$ and R$^c$ is -alkyl-NR$^f$R$^g$. In a still further embodiment, the other of R$^b$ and R$^c$ is —(C=O)—NR$^f$R$_g$, such as aminocarbonyl. In a further embodiment, the other of R$^b$ and R$^c$ is —O—NR$^f$R$^g$. In a still further embodiment, the other of R$^b$ and R$^c$ is —O-alkyl-NR$^f$R$^g$. In a further embodiment, the other of R$^b$ and R$^c$ is —NR$^h$-alkyl-N$^f$R$^g$. In a special embodiment, the other of R$^b$ and R$^c$ is amino, dimethylamino, methylamino or ethylamino. In a further special embodiment, the other of R$^b$ and R$^c$ is 1,2,3,6-tetrahydropyridin-1-ylmethyl, 1-ethylpiperazin-4-yl-methyl, morpholin-4-yl-methyl or 2-(morpholin-4-yl)ethoxy.

In a further embodiment, R$^b$ and R$^c$ together represent —O—CH$_2$—O—. Thus, R$^7$ is 3,4-methylenedioxyphenyl.

In a still further embodiment, R$^7$ is
—NR$^h$—(C=O)—R$^i$, —N=CH—R$^i$, or —C≡C—R$^i$;
wherein R$^h$ is hydrogen or alkyl; and
R$^i$ is alkyl or phenyl, which alkyl or phenyl is optionally substituted with hydroxy, trifluoromethyl, cyano or alkyl; or
—NR$^j$R$^k$, -alkyl-NR$^j$R$^k$, —CH=CH—(C=O)—NR$^j$R$^k$, —CH=CH—(C=O)—O-alkyl, -alkyl-(C=O)—NR$^j$R$^k$, or —C=CH$_2$—NR$^j$R$^k$;
wherein R$^j$ and R$^k$ independently of each other are selected from the group consisting of hydrogen, alkyl, -alkyl-CN, -alkyl-R'R" and -alkyl-R$^i$;
wherein R' and R" independently of each other are hydrogen or alkyl;
R$^i$ is a 5- to 7-membered heterocyclic ring comprising one nitrogen atom,
which heterocyclic ring may optionally comprise as a ring member, one oxygen atom, and/or one additional nitrogen atom, and/or one carbon-carbon double bond, and/or one carbon-nitrogen bond; and
which heterocyclic ring may optionally be substituted with trifluoromethyl, alkyl, hydroxyalkyl, or —NR'R";

wherein R' and R" independently of each other are hydrogen or alkyl;
or R$^j$ and R$^k$ together with the nitrogen to which they are attached form
a 5- to 7-membered heterocyclic ring,
which heterocyclic ring may optionally comprise as a ring member, one oxygen atom, and/or one additional nitrogen atom, and/or one carbon-carbon double bond, and/or one carbon-nitrogen bond; and
which heterocyclic ring may optionally be substituted with trifluoromethyl, alkyl, hydroxy, hydroxyalkyl, or —NR'R";
wherein R' and R" independently of each other are hydrogen or alkyl.

In a further embodiment, R$^7$ is —NR$^h$—(C=O)—R$^i$, such as acetamido.

In a still further embodiment, R$^7$ is —N=CH—R$^i$, such as benzylideneamino, 4-cyanobenzylideneamino or 3-cyanobenzylideneamino.

In a further embodiment, R$^7$ is or —C≡CH—R$^i$, such as 4-hydroxy-butyn-1-yl.

In a still further embodiment, R$^7$ is —NR$^j$R$^k$, such as 4-morpholinyl, N-methyl-N-(4-hydroxyethylpiperazin-1-yl-ethyl)-amino, N-methyl-N-(4-methylpiperazin-1-yl-ethyl)-amino or 3-dimethylamino-pyrrolidin-1-yl.

In a further embodiment, R$^7$ is -alkyl-NR$^j$R$^k$, such as diethylaminopropyl or N-methyl-N-(cyanoethyl)-aminobutyl.

In a still further embodiment, R$^7$ is —CH=CH—(C=O)—NR$^j$R$^k$, such as 3-(diethylamino)-propen-3-one-1-yl, 3-(4-methylpiperazin-1-yl)-propen-3-one-1-yl, 3-(piperidin-1-yl)-propen-3-one-1-yl, 3-(morpholin-4-yl)-propen-3-one-1-yl, 3-(homopiperazin-4-yl)-propen-3-one-1-yl, 3-(cyanoethylamino)-propen-3-one-1-yl, 3-(propylamino)-propen-3-one-1-yl, 3-(dimethylaminoethylamino)-propen-3-one-1-yl, 3-(4-trifluoromethyl-piperidin-1-yl)-propen-3-one-1-yl, 3-(pyrrolidin-1-yl)-propen-3-one-1-yl, 3-(2,5-dihydropyrrol-1-yl)-propen-3-one-1-yl, N-ethyl-N-isopropyl-carbamoyl-ethenyl, 1-methylpiperidineyl-methyl-carbamoyl-ethenyl, N-methyl-N-(1-methylpyrrolidin-3-yl)-carbamoyl-ethenyl, N-methyl-N-(1-methylpiperidine-4-yl)-carbamoyl-ethenyl or N-methyl-N-(cyanoethyl)-carbamoyl-ethenyl.

In a still further embodiment, R$^7$ is —CH=CH—(C=O)—O-alkyl, such as acetonylidenemethyl.

In a further embodiment, R$^7$ is -alkyl-(C=O)—NR$^j$R$^k$, such as N,N-diethylcarbamoylethyl.

In a still further embodiment, R$^7$ is —C≡C—CH$_2$—NR$^j$R$^k$, such as 3-(morpholin-4-yl)-propyn-1-yl, 3-(piperidin-1-yl)-propyn-1-yl or 3-(1-(1,2,3,6-tetrahydropyridinyl))propyn-1-yl.

In a further embodiment, R$^7$ is a heteroaryl group which heteroaryl group is optionally substituted with one or more substituents independently selected from the group consisting of: halo, trifluoromethyl, trifluoromethoxy, cyano, nitro, alkyl, and alkoxy.

In a still further embodiment, R$^7$ is indolyl, pyridyl or furyl optionally substituted halo or methyl. In a special embodiment, R$^7$ is selected from 1-Methyl-5-indolyl, pyridin-4-yl, pyridin-3-yl or 3-chloro-pyridin-4-yl.

In a special embodiment the chemical compound of the invention is 7-(3-Chlorophenyl)-1-phenyl-5-trifluoromethylbenzimidazole;

7-(3-Aminophenyl)-5-formyl-1-phenylbenzimidazole oxime;

O-Methyl 7-(3-Aminophenyl)-5-formyl-1-phenylbenzimidazole oxime;
7-(N-benzylideneamino)-1-phenyl-5-trifluoromethylbenzimidazole;
7-(N-(4-cyanobenzylidene)amino)-1-phenyl-5-trifluoromethylbenzimidazole;
7-(N-(3-cyanobenzylidene)amino)-1-phenyl-5-trifluoromethylbenzimidazole;
7-(3-Aminophenyl)-5-cyano-1-phenylbenzimidazole;
7-(3-(Hydroxymethyl)phenyl)-1-phenyl-5-trifluoromethylbenzimidazole;
1-Phenyl-7-(3-(1,2,3,6-tetrahydropyridine-1-ylmethyl)phenyl)-5-trifluoromethyl-benzimidazole;
7-(3-Acetamidophenyl)-5-ethoxycarbonyl-1-phenylbenzimidazole;
7-(3-Aminophenyl)-5-ethoxycarbonyl-1-phenylbenzimidazole;
5-(Ethoxycarbonyl)-7-(3-(hydroxymethyl)phenyl)-1-phenylbenzimidazole;
7-(3-Cyanophenyl)-1-phenyl-5-trifluorophenylbenzimidazole;
5-Cyano-7-(3-nitrophenyl)-1-phenylbenzimidazole;
5-Cyano-7-(3-hydroxymethylphenyl)-1-phenylbenzimidazole;
5-Cyano-7-(3-((1-methylpiperazin-4-yl)methyl)phenyl)-1-phenylbenzimidazole;
5-Cyano-7-(3-(diethylaminomethyl)phenyl)-1-phenylbenzimidazole;
7-(3-Acetamidophenyl)-5-cyano-1-phenylbenzimidazole;
5-Cyano-7-(4-methoxyphenyl)-1-phenylbenzimidazole;
5-Cyano-7-(3-methoxyphenyl)-1-phenylbenzimidazole;
5-Cyano-7-(4-cyanophenyl-1-phenylbenzimidazole;
5-Cyano-7-(3-fluorophenylyl)-1-phenylbenzimidazole;
5-Cyano-7-(4-hydroxyphenyl)-1-phenylbenzimidazole;
5-Cyano-7-[3-(dimethylamino)phenyl]-1-phenylbenzimidazole;
5-Cyano-7-(3,4-methylenedioxyphenyl)-1-phenyl benzimidazole;
5-Cyano-7-(pyridinyl)-1-phenylbenzimidazole;
7-(3-Aminophenyl)-5-hydroxymethyl-1-phenylbenzimidazole;
5-Ethoxycarbonyl-7-(3-((morpholin-4-yl)methyl)phenyl)-1-phenylbenzimidazole;
5-Ethoxycarbonyl-7-(3-((1-methylpiperazin-4-yl)methyl)phenyl)-1-phenylbenzimidazole;
5-Ethoxycarbonyl-7-(3-(((dimethylamino)methyl)phenyl)-1-phenylbenzimidazole;
5-Cyano-7-3-cyanophenylyl)-1-phenylbenzimidazole;
5-Cyano-7-(4-nitrophenyl)-1-phenylbenzimidazole;
7-(4-Acetamidophenyl)-5-cyano-1-phenylbenzimidazole;
7-(3-Acetamidophenyl)-1-phenyl-5-trifluoromethylbenzimidazole;
O-Methyl 7-(3-acetmidophenyl)-5-formyl-1-phenylbenzimidazole oxime;
O-Methyl 7-(3(dimethylamino)phenyl)-5-formyl-1-phenylbenzimidazole oxime;
5-Cyano-7-(4-diethylaminomethylphenyl)-1-phenylbenzimidazole;
7-(4-Benzamidyl)-5-cyano-1-phenylbenzimidazole;
7-(3-Acetamidophenyl)-5-hydroxymethyl-1-phenylbenzimidazole;
7-(3-Ethylaminophenyl)-5-hydroxymethyl-1-phenylbenzimidazole;
7-(3-Dimethylaminophenyl)-5-trifluoromethyl-1-phenylbenzimidazole;
7-(3-Methylaminophenyl)-5-trifluoromethyl-1-phenylbenzimidazole;
1-Phenyl-7-(3((4-methylpiperazin-1-yl)methyl)phenyl)-5-trifluoromethylbenzimidazole;
7-(3-(1-Morpholinylmethyl)phenyl)-1-phenyl-5-trifluoramethylbenzimidazole;
7-(3-((Dimethylamino)methyl)phenyl)-1-phenyl -5-trifluoromethylbenzimidazole;
5-Cyano-7-(4-(2-(4-morpholino)ethoxy)phenyl)-1-phenyl-benzimidazole;
7-(3-(N-Methyl acetamido)phenyl)-1-phenyl-5-trifluoromethylbenzimidazole;
1-Phenyl-7-(4-pyridyl)-5-trifluoromethylbenzimidazole;
5-(Hydroxymethyl)-1-phenyl-7-(3-trifluoromethoxyphenyl)benzimidazole;
7-(4-pyridyl N-oxide)-1-phenyl-5-trifluoromethylbenzimidazole;
7-(3-chloro-4-pyridyl)-1-phenyl-5-trifluoromethylbenzimidazole;
7-(3-chloro-4-pyridyl-N-oxide)-1-phenyl-5-trifluoromethylbenzimidazole;
7-(3-Acetylphenyl)-1-phenyl-5-trifluoromethylbenzimidazole;
7-(3-Fluorophenyl)-1-phenyl-5-trifluorophenylbenzimidazole;
3-(3-Phenyl-6-trifluoromethyl-3H-benzimidazol-4-yl)acrylic acid methyl ester;
3-(6-Cyano-3-phenyl-3H-benzimidazol-4-yl)acrylic acid methyl ester;
7-(4-Morpholinyl)-1-phenyl-5-trifluoromethylbenzimidazole;
5-t-Butyl-7-(3-dimethylaminophenyl)-1-phenylbenzimidazole;
7-(3-(1-Methoxyethyl)phenyl)-1-phenyl-5-trifluoromethylbenzimidazole;
7-(1-Methyl-5-indolyl)-1-phenyl-5-trifluoromethylbenzimidazole;
7-(3-(1-Hydroxyethyl)phenyl)-1-phenyl-5-trifluoromethylbenzimidazole;
7-(3-Furyl)-1-phenyl-5-trifluoromethylbenzimidazole;
N,N-Diethyl-3-(3-phenyl-6-trifluoromethyl-3H-benzimidazol-4-yl)acrylamide;
1-(4-Methylpiperazin-1-yl)-3-(3-phenyl-6-trifluoromethyl-3-H-benzimidazol-4-yl)prop-2-en-1-one;
3-(3-Phenyl-6-trifluoromethyl-3H-benzimidazol-4-yl)-1-piperidinylprop-2-en-1-one;
1-(4-Morpholinyl)-3-(3-phenyl-6-trifluoromethyl-3H-benzimidazol-4-yl)prop-2-en-1-one;
1-(4-Methyl-[1,4]-hexahydrodiazepin-1-yl)-3-(3-phenyl-trifluoromethyl-3H-benzimidazol-4-yl)prop-2-en-1-one;
N-(2-Cyanoethyl)-3-(3-phenyl-6-trifluoromethyl-3H-benzimidazol-4-yl)acrylamide;
3-(3-Phenyl-6-trifluoromethyl-3H-benzimidazol-4-yl)-N-propylacrylamide;
N-(2-Dimethylaminoethyl)-3-(3-phenyl-6-trifluoromethyl-3H-benzimidazol-4-yl)acrylamide;
3-(3-Phenyl-trifluoromethyl-3H-benzimidazol-4-yl)-1-(4-trifluoromethyl-piperidin-1-yl)prop-2-en-1-one;
7-(3-(2-Hydroxy-2-propyl)phenyl)-1-phenyl-5-trifluoromethylbenzimidazole;
7-(4-Hydroxypiperidinyl)-1-phenyl-5-trifluoromethylbenzimidazole;
7-(3-Fluorophenyl)-5-methyl-1-phenylbenzimidazole;
7-(4-Hydroxybut-1-ynyl)-1-phenyl-5-trifluoromethylbenzimidazole;
7-(1-(1-(4-Hydroxyethylpiperazinyl)ethyl)-1-methylamino)-1-phenyl-5-trifluoromethyl-benzimidazole;
7-(1-(1-(4-Methylpiperazinyl)ethyl)-1-methyl)amino-1-phenyl-5-trifluoromethyl-benzimidazole;

7-(3-(4-Morpholino)prop-1-ynyl)-1-phenyl-5-trifluorom-
ethylbenzimidazole;
N,N-Diethyl-3-(3-phenyl-6-trifluoromethyl-3H-benzimida-
zol-4-yl)propionamide;
3(6-tert-Butyl-3-phenyl-3H-benzimidazol-4-yl)-1-(piperi-
din-1-yl)prop-2-en-1-one;
N-Ethyl-N-isopropyl-3-(3-phenyl-6-trifluoromethyl-3H-
benzimidazol-4-yl )acrylamide;
N-(1-Methylpipeddin-4-yl)methyl-3-(3-phenyl-6-trifluo-
romethyl-3H-benzimidazol-yl)-acrylamide; N-Methyl-N-
(-methylpyrrolidin-3-yl)-3-(3-phenyl-6-trifluoromethyl-
3H-benzimidazol-4-yl)acrylamide;
3(6-tert-Butyl-3-phenyl-3H-benzimidazolyl)-N-methyl-N-
(1-methylpiperidin-4-yl)-acrylamide;
7-(4-(Diethylamino)-butyl)-phenyl-5-trifluoromethylbenz-
imidazole;
7-(4-((N-(2-Cyanoethyl)-N-methyl)amino)-1-butyl)-1-phe-
nyl-5-trifluoromethyl-benzimidazole;
3-(3-Phenyl-6-trifluoromethyl-3H-benzimidazol-4-yl)-1-
(pyrollidin-1-yl)prop-2-en-1-one;
1-(2,5-Dihydropyrrol-1-yl)-3-(3-phenyl-6-trifluoromethyl-
3H-benzimidazol-4-yl)prop-2-en-1-one;
N-(2-Cyanoethyl)-N-methyl-3-(3-phenyl-6-trifluoromethyl-
3H-benzimidazolyl)-acrylamide;
1-Phenyl-7-(3-(1-(1,2,3,6-tetrahydropyridinyl))prop-1-
ynyl)-5-trifluoromethylbenzimidazole;
1-Phenyl-7-(3-(1-piperidinyl)prop-1-ynyl-5-trifluorometh-
ylbenzimidazole;
7-[1-(3-Dimethylamino)pyrrolidinyl]-1-phenyl-5-trifluo-
romethylbenzimidazole;

or an N-oxide thereof, or any of its isomers or any mixture of its isomers, or a pharmaceutically acceptable salt thereof.

Any combination of two or more of the embodiments as described above is considered within the scope of the present invention.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to six carbon atoms ($C_{1-6}$-alkyl), including pentyl, isopentyl, neopentyl, tertiary pentyl, hexyl and isohexyl. In one embodiment alkyl represents a $C_{1-4}$-alkyl group, including butyl, isobutyl, secondary butyl, and tertiary butyl. In another embodiment of this invention alkyl represents a $C_{1-3}$-alkyl group, which may in particular be methyl, ethyl, propyl or isopropyl.

In the context of this invention an alkoxy group designates an "alkyl-O—" group, wherein alkyl is as defined above.

5- to 7-membered heterocyclic rings comprising one nitrogen atom include for example, but not limited to, pyrolidine, piperidine, homopiperidine, pyrroline, tetrahydropyridine, pyrazolidine, imidazolidine, piperazine, homopiperazine, and morpholine.

In the context of this invention a heteroaryl group designates an aromatic mono- or bicyclic heterocyclic group, which holds one or more heteroatoms in its ring structure. Preferred heteroatoms include nitrogen (N), oxygen (O), and sulphur (S).

Preferred monocyclic heteroaryl groups of the invention include aromatic 5- and 6 membered heterocyclic monocyclic groups, including for example, but not limited to, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1,2,5-thiadiazol-4-yl, 2-imidazolyl, 4-imidazolyl, 5-imidazolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidyl, 4-pyrimidyl, 5-pyrimidyl or 6-pyrimidyl.

Preferred bicyclic heteroaryl groups of the invention include indolizinyl, in particular 2-, 5- or 6-indolizinyl; indolyl, in particular 2-, 5- or 6-indolyl; isoindolyl, in particular 2-, 5- or 6-isoindolyl; benzo[b]furanyl, in particular 2-, 5- or 6-benzofuranyl; benzo[b]thienyl, in particular 2-, 5- or 6-benzothienyl; benzimidazolyl, in particular 2-, 5- or 6-benzimidazolyl; benzothiazolyl, in particular 5- or 6-benzothiazolyl; purinyl, in particular 2- or 8-purinyl; quinolinyl, in particular 2-, 3-, 6- or 7-quinolinyl; isoquinolinyl, in particular 3-, 6- or 7-isoquinolinyl; cinnolinyl, in particular 6- or 7-cinnolinyl; phthalazinyl, in particular 6- or 7-phthalazinyl; quinazolinyl, in particular 2-, 6- or 7-quinazolinyl; quinoxalinyl, in particular 2- or 6-quinoxalinyl; 1,8-naphthyridinyl, in particular 1,8-naphthyridin-2-, 3-, 6- or 7-yl; pteridinyl, in particular 2-, 6- or 7-pteridinyl; and indenyl, in particular 1-, 2-, 3-, 5- or 5-indenyl.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Examples of pre- or prodrug forms of the chemical compound of the invention include examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The chemical compound of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Steric Isomers

It will be appreciated by those skilled in the art that the compounds of the present invention may contain one or more chiral centres and that such compounds exist in the form of isomers.

The racemates of these isomers and the individual isomers themselves are within the scope of the present invention.

Methods for the resolution of optical isomers, known to those skilled in the art may be used, and will be apparent to the average worker skilled in the art. Such methods include those discussed by J. Jaques, A. Collet, and S. Wilen in "Enantiomers, Racemates, and Resolutions", John Wiley and Sons, New York (1981).

Optical active compounds can also be prepared from optical active starting materials.

N-oxides

In the context of this invention an N-oxide designates an oxide derivative of a nitrogen containing compound, e.g. N-containing heterocyclic compounds capable of forming such N-oxides, and compounds holding one or more amino groups. For example, the N-oxide of a compound containing a pyridyl may be the 1-oxy-pyridin-2, -3 or -4-yl derivative.

N-oxides of the compounds of the invention may be prepared by oxidation of the corresponding nitrogen base using a conventional oxidizing agent such as hydrogen peroxide in the presence of an acid such as acetic acid at an elevated temperature, or by reaction with a peracid such as peracetic acid in a suitable solvent, e.g. dichloromethane, ethyl acetate or methyl acetate, or in chloroform or dichloromethane with 3-chloroperoxybenzoic acid.

Labelled Compounds

The compounds of the invention may be used in their labelled or unlabelled form. In the context of this invention "label" stands for the binding of a marker to the compound of interest that will allow easy quantitative detection of said compound.

The labelled compounds of the invention may be useful as diagnostic tools, radio tracers, or monitoring agents in various diagnostic methods, and for in vivo receptor imaging.

The labelled isomer of the invention preferably contains at least one radionuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

The compounds of this invention may exist in unsolvated as well as in solvated forms with pharmaceutically acceptable solvents such as water, ethanol and the like. In general, the solvated forms are considered equivalent to the unsolvated forms for the purposes of this invention.

Biological Activity

Compounds of the invention are capable of modulating the $GABA_A$ receptor complex. They may be tested for their ability to bind to the $GABA_A$ receptor complex, including specific subunits thereof.

The compounds of the present invention, being ligands for $GABA_A$ receptors, are therefore of use in the treatment and/or prevention of a variety of disorders of the central nervous system. Thus in further aspect, the compounds of the invention are considered useful for the treatment, prevention or alleviation of a disease, disorder or condition responsive to modulation of the $GABA_A$ receptor complex in the central nervous system.

In a special embodiment, the compounds of the invention are considered useful for the treatment, prevention or alleviation of anxiety disorders, such as panic disorder with or without agoraphobia, agoraphobia without history of panic disorder, animal and other phobias including social phobias, obsessive-compulsive disorder, and generalized or substance-induced anxiety disorder;

stress disorders including post-traumatic and acute stress disorder;

sleep disorders;

memory disorder;

convulsive disorders, for example epilepsy, or febrile convulsions in children;

premenstrual syndrome;

muscle spasm or spasticity, e.g. in paraplegic patients;

the effects of substance abuse or dependency, including alcohol withdrawal; and disorders of circadian rhythm, e.g. in subjects suffering from the effects of jet lag or shift work.

The compounds of the invention may also be useful for:

inducing and maintaining anaesthesia, sedation and muscle relaxation; and pre-medication prior to anaesthesia or minor procedures such as endoscopy, including gastric endoscopy;

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Further, the compounds of the invention may be useful as radioligands in assays for detecting compounds capable of binding to the human $GABA_A$ receptor.

Pharmaceutical Compositions

In another aspect the invention provides novel pharmaceutical compositions comprising a therapeutically effective amount of a compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising a compound of the invention, or a pharmaceutically acceptable salt or derivative thereof, together with one or more pharmaceutically acceptable carriers therefore, and, optionally, other therapeutic and/or prophylactic ingredients, known and used in the art. The carrier(s) must be "acceptable" in the sense of being compatible with the other ingredients of the formulation and not harmful to the recipient thereof.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The chemical compound of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The chemical compound of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or with-out carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The chemical compound according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilizaton from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the chemical compound of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms-or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

EXAMPLES

The invention is further illustrated with reference to the following examples which are not intended to be in any way limiting to the scope of the invention as claimed.

Example 1

7-(3-Aminophenyl)-1-phenyl-5-trifluoromethylbenzimidazole

A mixture of 7-iodo-1-phenyl-5-trifluoromethylbenzimidazole (3.2 g, 8.2 mmol), 3-aminophenyl boronic acid (1.68 g, 12.3 mmol), sodium carbonate (5.68 g, 41 mmol), 1,3-propanediol (2.94 ml, 41 mmol) and bis(triphenylphosphin) palladium dichloride (200 mg, 0.28 mmol) in a mixture of water (13 ml) and dimethoxyethane (26 ml) was stirred at reflux overnight The cooled reaction mixture was partitioned between ethyl acetate and water, and the organic extract was purified by column chromatography on silica gel eluting with a mixture of dichloromethane and methanol (99:1, v/v). The product was isolated by removal of solvent from appropriate eluate fractions followed by crystallisation of the residue from 2-propanol (50 ml). Yield: 2.7 g (93%), m/z, 354.1 $(M+H)^+$.

Example 2

1-Phenyl-7-(3-pyridyl)-5-trifluoromethylbenzimidazole

A mixture of 7-iodo-1-phenyl-5-trifluoromethylbenzimidazole (370 mg, 1 mmol), diethyl 3-pyridylborane (220 mg, 1.5 mmol), sodium bicarbonate (420 mg, 5 mmol) and tetrakis(triphenylphosphine)palladium(0) (29 mg, 0.025 mmol) in a mixture of water (5 ml) and dimethoxyethane (10 ml) was stirred at reflux overnight The cooled reaction mixture was partitioned between ethyl acetate and water, and the organic extract was purified by column chromatography on silica gel eluting with a mixture of dichloromethane and acetone (9:1, v/v). The product was isolated by removal of solvent from appropriate eluate fractions followed by trituration of the residue with a mixture of water and ethanol. Yield: 130 mg (38%), m/z, 340.1 $(M+H)^+$.

Example 3

1.7-Diphenyl-5-trifluoromethylbenzimidazole

A mixture of 7-iodo-1-phenyl-5-trifluoromethylbenzimidazole (370 mg, 1 mmol), benzeneboronic acid (180 mg, 1.5 mmol), potassium carbonate (700 mg, 5 mmol) and tetrakis(triphenylphosphine)palladium(0) (29 mg, 0.025 mmol) in a mixture of water (5 ml) and dimethoxyethane (10 ml) was stirred at reflux overnight. The cooled mixture was partitioned between water and ethyl acetate. The organic phase was collected, washed with brine, dried and concentrated under reduced pressure. Recrystallisation from methanol afforded the product as an off-white solid (160 mg, 47%), m/z, 339.1 (M+H)$^+$.

Example 4

7-Benzoylamino-1-phenyl-5-trifluoromethylbenzimidazole

A mixture of 7-amino-1-phenyl-5-trifluoromethylbenzimidazole (300 mg, 1 mmol), benzoylchloride (0.23 ml, 2 mmol) and triethyl amine (0.3 ml, 2 mmol) in tetrahydrofurane (10 ml) was stirred at ambient temperature overnight. The solvent was removed under reduced pressure and the residue was partitioned between ethyl acetate and hydro chloric acid (4M). The aqueous phase was rendered alkaline with saturated, aqueous sodium carbonate and extracted with ethyl acetate. The extract was dried and concentrated under reduced pressure and the resultant gum was triturated with a mixture of diethyl ether and petroleum ether to leave the solid, off-white product (145 mg, 38%), m/z, 382.1 (M+H)$^+$.

Example 5

7-(3-Chlorophenyl)-1-Phenyl-5-trifluoromethylbenzimidazole

A mixture of 7-iodo-1-phenyl-5-trifluoromethylbenzimidazole (1.0 g, 2.6 mmol), 3-chlorobenzeneboronic acid (0.6 g, 3.87 mmol), 1,3-propanediol (1 ml, 12.9 mmol), potassium carbonate (1.8 g, 12.9 mmol) and bis(triphenylphosphin)palladium dichloride (100 mg, 0.14 mmol) was stirred at reflux for one hour. The cooled mixture was partitioned between water and ethyl acetate. The organic extract was dried and concentrated under reduced pressure. The concentrate was purified by chromatography on silica gel eluting with a mixture of ethyl acetate and ligroin (2:3, v/v). Removal of solvent left the desired product as a white solid (0.9 g, 94%) m/z, 373.1 (M+H)$^+$.

Example 6

7-(3-Aminophenyl)-5-formyl-1-phenylbenzimidazole oxime

To a solution of 7-(3-aminophenyl)-5-cyano-1-phenylbenzimidazole (3.4 g, 11.0 mmol) in a mixture of formic acid (70 ml) and water (23 ml), saturated with nitrogen, was added Raney nickel (3 g) and the resultant mixture was stirred at reflux for 1 hour. The hot reaction mixture was filtered through a pad of celite, which was washed with water. The filtrate was concentrated under reduced pressure and the concentrate was partitioned between saturated, aqueous sodium carbonate and ethyl acetate. The organic phase was purified by column chromatography on silica gel eluting with a mixture of ethyl acetate and methanol (9:1 v/v) to yield 7-(3-(formylamino)phenyl)-5-formyl-1-phenylbenzimidazole as a yellowish solid (1 g, 27%).

The above intermediate (0.4 g, 1.17 mmol) was suspended in abs. ethanol (10 ml) and hydroxylamine hydrochloride (0.12 g, 1.76 mmol) was added. The resultant mixture was stirred at reflux for 1 hour. The crude product, which precipitated upon cooling, was filtered off and washed successively with aqueous sodium carbonate, water and ethanol. Column chromatography on silica gel eluting with ethyl acetate left the title product as white crystals (50 mg, 13%) m/z, 329.1 (M+H)$^+$.

Example 7

O-Methyl 7-(3-Aminophenyl)-5-formyl-1-phenylbenzimidazole oxime

This was prepared analogously to the above product from 7-(3-(formylamino)phenyl)-5-formyl-1-phenylbenzimidazole (0.4 g, 1.17 mmol) and O-methyl hydroxylamine hydrochloride (0.15 g, 1.76 mmol). The product was obtained as a white solid (0.3 g, 74%) m/z, 343.2 (M+H)$^+$.

Example 8

7-(N-benzylideneamino)-1-phenyl-5-trifluoromethylbenzimidazole

To a solution of 7-amino-1-phenyl-5-trifluoromethylbenzimidazole (0.50 g, 1.81 mmol) in anhydrous toluene (10 ml) was added benzaldehyde, p-toluenesulphonic acid (10 mg) and molecular sieves. The resultant mixture was stirred at reflux for 1.5 hours. The molecular sieves were removed by filtration and the filtrate was concentrated under reduced pressure. The concentrate was partitioned between aqueous sodium carbonate (2M) and ethyl acetate. The organic phase was dried and concentrated, and the concentrate was eluted through silica gel with a mixture of ethyl acetate and ligroin (1:1 v/v). Removal of solvent from the eluate left the desired product as a yellow solid (0.37 g, 56%) m/z, 366.1 (M+H)$^+$.

Example 9

7-(N-(4 cyanobenzylidene)amino-1-phenyl-5-trifluoromethylbenzimidazole

This was prepared analogously to the above product from 7-amino-1-phenyl-5-trifluoromethylbenzimidazole (1.09, 3.61 mmol) and 4-cyanobenzaldehyde (0.47 g, 3.61 mmol) yielding 0.96 g (68%) m/z, 391.1 (M+H)$^+$.

Example 10

7-(N-(3-cyanobenzylidene)amino)-1-phenyl-5-trifluoromethylbenzimidazole

This was prepared analogously to the above product from 7-amino-1-phenyl-5-trifluoromethylbenzimidazole (1.0 g, 3.61 mmol) and 3-cyanobenzaldehyde (0.47 g, 3.61 mmol) yielding 0.90 g (64%) m/z, 391.1 (M+H)$^+$.

Example 11

7-(3-Aminophenyl)-5-cyano-1-Phenylbenzimidazole

A mixture of 5-cyano-7-iodo-1-phenylbenzimidazole (1.9 g, 5.5 mmol), 3-aminophenylboronic acid hemisulphate (1.53 g, 8.3 mmol), 1,3-propanediol (2 ml, 27.5 mmol), potassium carbonate (3.8 g, 27.5 mmol) and bis(triphenylphosphin)palladium dichloride (100 mg, 0.14 mmol) in a mixture of dimethoxyethane (20 ml) and water (10 ml) was stirred at reflux for 1 hour. The resultant mixture was poured into water and the crude product was filtered off, washed with water and air-dried. Trituration in dichloromethane offered the desired product as a greyish solid (1.5 g, 88%) m/z, 311.1 (M+H)$^+$.

Example 12

7-(3-(Hydroxymethyl)phenyl)-1-phenyl-5-trifluoromethylbenzimidazole

A mixture of 5-cyano-7-iodo-1-phenylbenzimidazole (1.0 g, 2.7 mmol), 3-(hydroxymethyl)phenylboronic acid (0.62 g, 4.1 mmol), 1,3-propanediol (0.97 ml, 13.5 mmol), potassium carbonate (1.87 g, 13.5 mmol) and bis(triphenylphosphin)palladium dichloride (50 mg, 0.07 mmol) in a mixture of dimethoxyethane (10 ml) and water (5 ml) was stirred at reflux for 1 hour. The cooled reaction mixture was concentrated under reduced pressure, and the concentrate was partitioned between water and ethyl acetate. The organic phase was dried and concentrated under reduced pressure, and the concentrate was crystallised from diethyl ether leaving the product as white crystals (660 mg, 66%) m/z, 369.1 (M+H)$^+$.

Example 13

1-Phenyl-7-(3-(1,2,3,6-tetrahydropydridine-1-ylmethyl)phenyl)-5-trifluoromethyl-benzimidazole A mixture of 7-(3-(hydroxymethyl)phenyl-1-phenyl-5-trifluoromethylbenzimidazole (0.55 g, 1.5 mmol), pyridine (1 ml) and p-toluenesulphonyl chloride (0.57 g, 3 mmol) was stirred at gentle reflux overnight. Ethyl acetate (5 ml) was added to the cooled mixture and the resultant precipitate was filtered off, washed with ethyl acetate and air-dried. This intermediate pyridinium sulphonate (1 g) was dissolved in dimethyl formamide (10 ml). Sodium borohydride (0.23 g, 6 mmol) was added and the resultant mixture was stirred at ambient temperature overnight. Aqueous calcium chloride (2M, 30 ml) was added carefully, and the resultant mixture was extracted with ethyl acetate. The organic extract was washed with brine, dried over magnesium sulphate and concentrated under reduced pressure. The residue was purified on silica gel eluting with ethyl acetate. Removal of solvent from the eluate and crystallisation from 2-propanol afforded the desired product (15 mg, 2%) m/z, 434.2 (M+H)$^+$.

Example 14

7-(3-Acetamidophenyl)-5-ethoxycarbonyl-1-phenyl-benzimidazole

A mixture of 5-ethoxycarbonyl-7-iodo-1-phenylbenzimidazole (0.70 g, 1.8 mmol), 3-acetamidophenylboronic acid (0.48 g, 2.7 mmol), 1,3-propanediol (0.65 ml, 8.9 mmol), potassium carbonate (1.23 g, 8.9 mmol) and bis(triphenylphosphin)palladium dichloride (50 mg, 0.07 mmol) in a mixture of dimethoxyethane (10 ml) and water (5 ml) was stirred at reflux for 1 hour. The cooled reaction mixture was concentrated under reduced pressure, and the concentrate was partitioned between water and ethyl acetate. The organic phase was dried and concentrated under reduced pressure, and the concentrate was triturated in ethyl acetate leaving the product as an off-white solid (0.48 g, 67%) m/z, 400.2 (M+H)$^+$.

Example 15

7-(3-Aminophenyl)-5-ethoxycarbonyl-1-phenylbenzimidazole

This was prepared analogously to the above product from 5-ethoxycarbonyl-7-iodo-1-phenylbenzimidazole (2.1 g, 5.36 mmol), 3-aminophenylboronic acid (1.1 g, 8.04 mmol), 1,3-propanediol (1.9 ml, 26.8 mmol), potassium carbonate (3.7 g, 26.8 mmol) and bis(triphenylphosphin)palladium dichloride (50 mg, 0.07 mmol) in a mixture of dimethoxyethane (10 ml) and water (5 ml). The title product was obtained as an off-white solid (1.30 g, 68%) m/z, 358.2 (M+H)$^+$.

Example 16

5-(Ethoxycarbonyl)-7-(3-(hydroxymethyl)phenyl)-1-phenylbenzimidazole

This was prepared analogously to 7-(3-acetamidophenyl)-5-ethoxycarbonyl-1-phenylbenzimidazole from 5-ethoxycarbonyl-7-iodo-1-phenylbenzimidazole (2.7 g, 6.89 mmol), 3-(hydroxymethyl)phenylboronic acid (1.57 g, 10.3 mmol), 1,3-propanediol (2.5 ml, 34.4 mmol), potassium carbonate (4.75 g, 34.4 mmol) and bis(triphenylphosphin)palladium dichloride (100 mg, 0.14 mmol) in a mixture of dimethoxyethane (30 ml) and water (15 ml). The title product was obtained as an off-white solid (2.1 g, 82%) m/z, 373.2 (M+H)$^+$.

Example 17

7(3-Cyanophenyl)-1-phenyl-5-trifluorophenylbenzimidazole

A mixture of 7-iodo-1-phenyl-5-trifluoromethylbenzimidazole (3.1 g, 8 mmol), 3-cyanophenylboronic acid (1.76 g, 12 mmol), 1,3-propanediol (2.9 ml, 40 mmol), potassium carbonate (5.54 g, 40 mmol) and bis(triphenylphosphin)palladium dichloride (200 mg, 0.28 mmol) in a mixture of dimethoxyethane (30 ml) and water (15 ml) was stirred at reflux for 4 hours. The cooled reaction mixture was concentrated under reduced pressure, and the concentrate was partitioned between water and ethyl acetate. The organic phase was dried and concentrated under reduced pressure, and the concentrate was purified by column chromatography on silica gel eluting with a mixture of ligroin and ethyl acetate (1:1 v/v). The product was isolated by evaporation of solvent from the eluate, and crystallised by trituration with diethyl ether (0.78 g, 27%) m/z, 364.1 (M+H)$^+$.

Example 18

5-Cyano-7-(3-nitrophenyl)-1-phenylbenzimidazole

This was prepared from 5-cyano-7-iodo-1-phenylbenzimidazole (173 mg, 0.5 mmol), toluene (3.0 ml), tetrakis(triphenylphosphine)palladium(0) (58 mg, 0.05 mmol), 3-nitrophenylboronic acid (84 mg, 0.5 mmol), ethanol (3.0 ml) and potassium carbonate (138 mg, 1.0 mmol) in a similar manner to 7-(3-acetamidophenyl)-5-cyano-1-phenylbenzimidazole.

Purification by a similar procedure afforded the title compound (13 mg, 8%) m/z, 341.0 (M+H)⁺.

Example 19

5-Cyano-7-(3-hydroxymethylphenyl)-1-phenylbenzimidazole trifluoracetic acid salt 5-Cyano-7-iodo-1-phenylbenzimidazole (173 mg, 0.5 mmol), toluene (3.0 ml), tetrakis(triphenylphosphine)palladium(0) (58 mg, 0.05 mmol), 3-hydroxymethylphenyl-boronic acid (76 mg, 0.5 mmol), ethanol (3.0 ml) and potassium carbonate (2M in water, 0.5 ml, 138 mg, 1.0 mmol) were added sequentially to a tube under nitrogen and refluxed for 22 h. The tube was blown dry with nitrogen and the solid residue washed (trifluoroacetic acid in acetonitrile, 0.1%, 3 times 1.5 ml). The liquid was evaporated and the resulting solid dissolved in dichloromethane/methanol (19:1) and eluted through an SPE column (C18, Isolute, 2 g, 6 ml) to give a solid (190 mg). This solid was dissolved in dimethylsulphoxide (2 ml) and eluted through a prep LCMS column to give, after removal of the solvent, the desired product as a glass (70 mg, 32%) m/z, 326.3 (M+H)⁺.

Example 20

5Cyano-7-(3-((1-methylpiperazin-4-yl)methyl)phenyl)-1-phenylbenzimidazole trifluoroacetic acid salt 5-Cyano-7-iodo-1-phenylbenzimidazole (1.0 g, 2.90 mmol), 3-hydroxymethyl-phenylboronic acid (440 mg, 2.90 mmol) and tetrakis(triphenylphosphine)palladium(0) (330 mg, 2.90 mmol) were dissolved in toluene (8.0 ml) and ethanol (2.0 ml). Potassium carbonate (2M in water, 2.9 ml, 800 mg, 5.8 mmol) was added and the reaction mixture heated at reflux under a nitrogen atmosphere for 16 h. The reaction mixture was passed through a plug of silica gel using dichloromethane/methanol (19:1) to elute. The organic phase was concentrated under reduced pressure and the resultant gum triturated with ethyl acetate and dichloromethane. 5-Cyano-7-(3-hydroxymethylphenyl)-1-phenylbenzimidazole was obtained as an off-white solid (500 mg, 39%) m/z, 326.2 (M+H)⁺.

5-Cyano-7-(3-hydroxymethylphenyl)-1-phenylbenzimidazole (500 mg, 1.54 mmol) was dissolved in dichloromethane (10 ml) and cooled to 0° C. Diisopropylethylamine (0.82 ml, 4.62 mmol) and methanesulphonyl chloride (0.13 ml, 1.69 mmol) were added sequentially and the reaction mixture stirred at room temperature for 1 h. The crude solution (approximately 0.14 M of product) was used directly in the next stage.

Crude 5-cyano-7-(3-methanesulphonylmethylphenyl)-1-phenylbenzimidazole (2.0 ml, 0.14 M solution in dichloromethane) was added to N-methylpiperazine (0.044 ml, 0.40 mmol) in dichloromethane (2 ml). The reaction mixture was stirred at room temperature for 12 h then the solvent removed under reduced pressure. Purification by prep LCMS gave the title compound as a clear, colourless glass (43 mg, 7%) m/z, 408.6 (M+H)⁺.

Example 21

5-Cyano-7-(3-(diethylaminomethyl)phenyl)-1-phenylbenzimidazole trifluoroacetic acid salt Prepared as for 5-cyano-7-(3-(1-methylpiperazin-4-yl)methylphenyl)-1-phenylbenzimidazole, using 5-cyano-7-(3-methanesulphonylmethylphenyl)-1-phenylbenzimidazole (2.0 ml, 0.14 M solution in dichloromethane) and diethylamine (0.041 ml, 0.40 mmol) as starting materials. Purification by prep LCMS gave the title compound as a clear, colourless glass (43 mg, 7%) m/z, 381.4 (M+H)⁺.

Example 22

7-(3-Acetamidophenyl)-5-cyano-1-phenylbenzimidazole

5-Cyano-7-iodo-1-phenylbenzimidazole (173 mg, 0.5 mmol), toluene (3.0 ml), tetrakis(triphenylphosphine)palladium(0) (58 mg, 0.05 mmol), 3-acetamidophenylboronic acid (90 mg, 0.5 mmol), ethanol (3.0 ml) and potassium carbonate (138 mg, 1.0 mmol) were combined and the mixture was stirred at reflux overnight. The solvent was removed under reduced pressure and the crude product was purified on a 2 g silica Isolute® SPE column, eluting with dichloromethane/methanol (98:2). The eluent from this column was evaporated under reduced pressure and the crude product was purified further by prep LCMS, then recrystallised from dichloromethane/diethyl ether to give the product as a white solid (64 mg, 36%) m/z, 353.0 (M+H)⁺.

Example 23

5-Cyano-7-(4-methoxyphenyl)-1-phenylbenzimidazole

This was prepared from 5-cyano-7-iodo-1-phenylbenzimidazole (173 mg, 0.5 mmol), toluene (3.0 ml), tetrakis(triphenylphosphine)palladium(0) (58 mg, 0.05 mmol), 4-methoxyphenylboronic acid (76 mg, 0.5 mmol), ethanol (3.0 ml) and potassium carbonate (138 mg, 1.0 mmol) In a similar manner to 7-(3-acetamidophenyl)-5-cyano-1-phenylbenzimidazole. Purification by a similar procedure afforded the title compound (47 mg, 29%) m/z, 326.5 (M+H)⁺.

Example 24

5-Cyano-7-(3-methoxyphenyl)-1-phenylbenzimidazole

This was prepared from 5-cyano-7-iodo-1-phenylbenzimidazole (173 mg, 0.5 mmol), toluene (3.0 ml), tetrakis(triphenylphosphine)palladium(0) (58 mg, 0.05 mmol), 3-methoxyphenylboronic acid (76 mg, 0.5 mmol), ethanol (3.0 ml) and potassium carbonate (138 mg, 1.0 mmol) in a similar manner to 7-(3-acetamidophenyl)-5-cyano-1-phenylbenzimidazole. Purification by a similar procedure afforded the title compound (51 mg, 31%) m/z, 326.5 (M+H)⁺.

Example 25

5-Cyano-7-(4 cyanophenyl)-1-phenylbenzimidazole

This was prepared from 5-cyano-7-iodo-1-phenylbenzimidazole (173 mg, 0.5 mmol), toluene (3.0 ml), tetrakis(triphenylphosphine)palladium(0) (58 mg, 0.05 mmol), 4-cyanophenylboronic acid (74 mg, 0.5 mmol), ethanol (3.0 ml) and potassium carbonate (138 mg, 1.0 mmol) in a similar manner to 7-(3-acetamidophenyl)-5-cyano-1-phenylbenzimidazole. Purification by a similar procedure afforded the title compound (94 mg, 59%) m/z, 321.0 (M+H)⁺.

Example 26

5Cyano-7-(3-fluorophenyl)-1-Phenylbenzimidazole

This was prepared from 5-cyano-7-iodo-1-phenylbenzimidazole (173 mg, 0.5 mmol), toluene (3.0 ml), tetrakis(triphenylphosphine)palladium(0) (58 mg, 0.05 mmol), 3-fluorophenylboronic acid (70 mg, 0.5 mmol), ethanol (3.0 ml) and potassium carbonate (138 mg, 1.0 mmol) in a similar manner to 7-(3-acetamidophenyl)-5-cyano-1-phenylbenzimidazole. Purification by a similar procedure afforded the title compound (67 mg, 43%) m/z, 314.0 (M+H)⁺.

Example 27

5-Cyano-7-(4-hydroxyphenyl)-1-phenylbenzimidazole

This was prepared in a similar manner to 5-cyano-7-(3-hydroxymethylphenyl)-1-phenylbenzimidazole, with 90 h reflux before removal of solvent using nitrogen to give an oily residue. The residue was taken up in acetonitrile (3 ml) and the resulting solid filtered off and dried under reduced pressure to give the desired product (490 mg, 77%) m/z, 312.3 (M+H)⁺.

Example 28

5-Cyano-7-[3-(dimethylamino)phenyl]-1-phenylbenzimidazole

5-Cyano-7-iodo-1-phenylbenzimidazole (173 mg, 0.5 mmol), toluene (3.0 ml), tetrakis(triphenylphosphine)palladium(0) (58 mg, 0.05 mmol), 3-dimethylaminophenylboronic acid (82 mg, 0.5 mmol), ethanol (3.0 ml) and potassium carbonate (138 mg, 1.0 mmol) were combined and the mixture was stirred at reflux overnight. The solvent was removed under reduced pressure and crude product was purified on a 2 g silica Isolute® SPE column, eluting with dichloromethane/methanol (95:5). The eluent was concentrated under reduced pressure and the crude product was suspended in acetonitrile then treated with diethyl ether to precipitate the product Recrystallisation from diethyl ether afforded the title compound (64 mg, 38%) m/z, 339.0 (M+H)⁺.

Example 29

5-Cyano-7-(3,4-methylenedioxyphenyl)-1-phenylbenzimidazole

5-Cyano-7-iodo-1-phenylbenzimidazole (173 mg, 0.5 mmol), toluene (3.0 ml), tetrakis(triphenylphosphine)palladium(0) (58 mg, 0.05 mmol), 3,4-methylene dioxyphenylboronic acid (83 mg, 0.5 mmol), ethanol (3.0 ml) and potassium carbonate (138 mg, 1.0 mmol) were combined and the mixture was stirred at reflux overnight The solvent was removed under reduced pressure and the crude product was purified on a 2 g silica Isolute® SPE column, eluting with dichloromethane/methanol (95:5). The eluent was concentrated under reduced pressure and product was crystallised from dichloromethane/diethyl ether to the title compound (75 mg, 44%) m/z, 339.8 (M+H)⁺.

Example 30

5-Cyano-7-(pyridin-4-yl)-1-phenylbenzimidazole

5-Cyano-7-iodo-1-phenylbenzimidazole (173 mg, 0.5 mmol), toluene (3.0 ml), tetrakis(triphenylphosphine)palladium(0) (58 mg, 0.05 mmol), pyridin-4-yl boronic acid (62 mg, 0.5 mmol), ethanol (3.0 ml) and potassium carbonate (138 mg, 1.0 mmol) were combined and the mixture was stirred at reflux overnight. The solvent was removed under reduced pressure and the crude product was purified on a 2 g silica Isolute® SPE column, eluting with dichloromethane/methanol (95:5). The eluent was concentrated under reduced pressure and the crude product was suspended in acetonitrile then treated with diethyl ether to precipitate the product. The mother liquors were removed by filtration and the residual solid was further purified on a Biotage silica gel cartridge, eluting with dichloromethane/methanol (98:2). Recrystallisation from dichloromethane/diethyl ether afforded the title compound (48 mg, 32%) m/z, 297.4 (M+H)⁺.

Example 31

7-(3-Aminophenyl)-5-hydroxymethyl-1-phenylbenzimidazole

To a stirred suspension of lithium alumina hydride (0.24 g, 6.16 mmol) in anhydrous diethyl ether (20 ml) was added 7-(3-aminophenyl)-5-ethoxycarbonyl-1-phenylbenzimidazole (1.1 g, 3.08 mmol). Stirring was continued for 48 hours at ambient temperature in a nitrogen atmosphere. Aqueous sodium bicarbonate (2M) was added and the resultant mixture was extracted with ethyl acetate. This extract was dried over magnesium sulphate and concentrated under reduced pressure. The concentrate was eluted through silica gel with a mixture of ethyl acetate and methanol (9:1 v/v). Removal of solvent from the eluate left the title product as a yellow solid (0.38 g, 39%) m/z, 316.1 (M+H)⁺.

Example 32

5-Ethoxycarbonyl-7-(3-((morpholin-4-yl)methyl)phenyl)-1-phenylbenzimidazole

To a stirred suspension of 5-ethoxycarbonyl-7-(3-(hydroxymethyl)phenyl)-1-phenylbenzimidazole (1.7 g, 4.57 mmol) in anhydrous toluene (20 ml) was added thionyl chloride (0.80 ml, 10.96 mmol) and stirring was continued at ambient temperature overnight. Excess thionyl chloride and toluene was removed by evaporation under reduced pressure. The intermediate 5-ethoxycarbonyl-7-(3-(chloromethyl)phenyl)-1-phenylbenzimidazole precipitated from the residue upon trituration with ethyl acetate (1.56 g).

This intermediate (0.5 g, 1.28 mmol) was dissolved in dimethyl formamide (5 ml) and morpholine (0.44 ml, 5.12 mmol) was added. The resultant mixture was stirred at 80° C. overnight whereupon water was added, causing a crude product to precipitate. The precipitate was filtered off and purified by column chromatography on silica gel eluting with ethyl acetate. Removal of solvent from the eluate left the title product as a colourless gum. This gum was redissolved in anhydrous diethyl ether and etheral hydrochloric acid (0.5 ml, 2M) was added to afford the desired product as the HCl salt (0.40 g, 71%) m/z, 422.2 (M+H)$^+$.

Example 33

5-Ethoxycarbonyl-7-(3-((1-methylpiperazin-4-yl) methyl)phenyl)-1-phenylbenzimidazole This was prepared analogously to the above product from 5-ethoxycarbonyl-7-(3-(chloromethyl)phenyl)-1-phenylbenzimidazole (0.50 g, 1.28 mmol) and 1-methylpiperazine (0.50 g, 3.84 mmol) in anhydrous dimethylformamide (5 ml) affording the title product as the hydrochloride (0.5 g, 80%) m/z, 455.2 (M+H)$^+$.

Example 34

5-Ethoxycarbonyl-7-(3-((dimethylamino)methyl) phenyl)-1-phenylbenzimidazole

This was prepared analogously to 5-Ethoxycarbonyl-7-(3-(morpholin-4-yl-methyl)phenyl)-1-phenylbenzimidazole from 5-ethoxycarbonyl-7-(3-(chloromethyl)phenyl)-1-phenylbenzimidazole (0.50 g, 1.28 mmol) and dimethylamine (approximately 2 ml) in anhydrous dimethylformamide (5 ml). The crude product was triturated in diethyl ether to afford the title product as an off-white solid (0.139, 25%) m/z, 400.2 (M+H)$^+$.

Example 35

5-Cyano-7-(3-cyanophenyl)-1-phenylbenzimidazole

5-Cyano-7-iodo-1-phenylbenzimidazole (173 mg, 0.5 mmol), toluene (3.0 ml), tetrakis(triphenylphosphine)palladium(0) (58 mg, 0.05 mmol), 3-cyanophenylboronic acid (73 mg, 0.5 mmol), ethanol (3.0 ml) and potassium carbonate (138 mg, 1.0 mmol) were combined and the mixture was stirred at reflux overnight. The solvent was removed under reduced pressure and the crude product was purified on a 2 g silica Isolute® SPE column, eluting with dichloromethane/methanol (95:5). The eluent was concentrated under reduced pressure and the crude product was purified by reverse-phase prep LCMS to give the title compound (9.3 mg, 6%) m/z, 321.2 (M+H)$^+$.

Example 36

5-Cyano-7-(4-nitrophenyl)-1-phenylbenzimidazole

This was prepared from 5-cyano-7-iodo-1-phenylbenzimidazole (173 mg, 0.5 mmol), toluene (3.0 ml), tetrakis(triphenylphosphine)palladium(0) (58 mg, 0.05 mmol), 4-nitrophenylboronic add (84 mg, 0.5 mmol), ethanol (3.0 ml) and potassium carbonate (138 mg, 1.0 mmol) in a similar manner to 7-(3-acetamidophenyl)-5-cyano-1-phenylbenzimidazole. Purification by a similar procedure afforded the title compound (56 mg, 33%) m/z, 341.0 (M+H)$^+$.

Example 37

7-(4-Acetamidophenyl)-5-cyano-1-phenylbenzimidazole

This was prepared from 5-cyano-7-iodo-1-phenylbenzimidazole (173 mg, 0.5 mmol), toluene (3.0 ml), tetrakis(triphenylphosphine)palladium(0) (58 mg, 0.05 mmol), 4-acetamidophenylboronic acid (90 mg, 0.5 mmol), ethanol (3.0 ml) and potassium carbonate (138 mg, 1.0 mmol) in a similar manner to 7-(3-acetamidophenyl)-5-cyano-1-phenylbenzimidazole. Purification by a similar procedure afforded the title compound (66 mg, 37%) m/z, 353.0 (M+H)$^+$.

Example 38

7-(3-Acetamidophenyl)-1-phenyl-5-trifluoromethylbenzimidazole

A solution of 7-(3-aminophenyl)-1-phenyl-5-trifluoromethylbenzimidazole (0.32 g, 0.9 mmol) in acetic anhydride (3 ml) was stirred at ambient temperature for one hour. Saturated, aqueous sodium carbonate was added and the resultant mixture was extracted with ethyl acetate. This organic extract was washed with water and brine, successively, dried over magnesium sulphate, concentrated under reduced pressure and purified by column chromatography on silica gel eluting with a mixture of dichloromethane and methanol (97:3, v/v) to afford the desired product (0.27 g, 76%) m/z, 396.1 (M+H)$^+$.

Example 39

O-Methyl 7-(3-acetmidophenyl)-5-formyl-1-Phenylbenzimidazole oxime

This was prepared from O-Methyl 7-(3-Aminophenyl)-5-formyl-1-phenylbenzimidazole oxime (70 mg, 0.2 mmol) by acetylation with acetic anhydride under standard conditions to afford the off-white solid product (44 mg, 57%) m/z, 385.2 (M+H)$^+$.

Example 40

O-Methyl 7-(3-(dimethylamino)phenyl)-5-formyl-1-phenylbenzimidazole oxime

This was prepared analogously to O-Methyl 7-(3-aminophenyl)-5-formyl-1-phenylbenzimidazole oxime from 5-cyano-7-(3-(dimethylamino)phenyl)-1-phenylbenzimidazole (0.4 g, 1.2 mmol), Raney Ni (0.6 g) in a mixture of formic acid (6 ml) and water (3 ml). The intermediate aldehyde was used without purification and treated with O-methyl hydroxylamine to afford the title product (30 mg, 14%) m/z, 371.2 (M+H)$^+$.

Example 41

5-Cyano-7-(4-diethylaminomethylphenyl)-1-phenylbenzimidazole trifluoroacetic acid salt 5-Cyano-7-(4-hydroxymethylphenyl)-1-phenylbenzimidazole was prepared from 5-cyano-7-iodo-1-phenylbenzimidazole (1.0 g, 2.90 mmol), 4-hydroxymethylphenylboronic acid (440 mg, 2.90 mmol), tetrakis(triphenylphosphine)palladium(0) (330 mg, 2.90 mmol) and potassium carbonate (2M in water, 2.9 ml, 800 mg, 5.8 mmol) in toluene (8.0 ml) and ethanol (2.0 ml) using the method described for 5-cyano-7-(3-hydroxymethylphenyl)-1-phenylbenzimidazole. 5-Cyano-7-(4-hydroxymethylphenyl)-1-phenylbenzimidazole was obtained as a white solid (711 mg) m/z, 326.3 (M+H)$^+$.

5-Cyano-7-(4-methanesulphonylmethylphenyl)-1-phenylbenzimidazole was prepared from 5-cyano-7-(4-hydroxymethylphenyl)-1-phenylbenzimidazole (500 mg, 1.54 mmol), diisopropylethylamine (0.82 ml, 4.62 mmol) and methanesulphonyl chloride (0.13 ml, 1.69 mmol) in dichloromethane (10 ml) using the method described for 5-cyano-7-(3-methanesulphonylmethylphenyl)-1-phenylbenzimidazole. The crude solution (approximately 0.14 M of product) was used directly in the next stage.

The title compound was prepared from 5-cyano-7-(4-methanesulphonylmethylphenyl)-1-phenylbenzimidazole (2.0 ml, 0.14 M solution in dichloromethane) and diethylamine (0.041 ml, 0.40 mmol) using the method described for 5-cyano-7-(3-diethylaminomethylphenyl)-1-phenylbenzimidazole. Purification by prep LCMS gave the title compound as a clear, colourless glass (38 mg, 7%) m/z, 381.4 (M+H)$^+$.

Example 42

7-(4-Benzamidyl)-5-cyano-1-Phenylbenzimidazole trifluoroacetic acid salt

This was prepared in a similar manner to 5-cyano-7-(3-hydroxymethylphenyl)-1-phenylbenzimidazole, with 70 h reflux before removal of solvent using nitrogen to give an oily residue. The residue was taken up in dimethylsulphoxide (2 ml) and eluted through a prep LCMS column to give, after removal of the solvent, the desired product as a glass (99 mg, 44%) m/z, 339.3 (M+H)$^+$.

Example 43

7-(3-Acetamidophenyl)-5-hydroxymethyl-1-phenyl-benzimidazole, and 7-(3-Ethylaminophenyl)-5-hydroxymethyl-1-Phenylbenzimidazole To a stirred solution of 7-(3-acetamidophenyl)-5-ethoxycarbonyl-1-phenylbenzimidazole (1.0 g, 2.51 mmol) in anhydrous tetrahydrofurane (50 ml) was added lithium aluminum hydride (0.2 g, 5 mmol). The resultant mixture was stirred at ambient temperature in a nitrogen atmosphere for 6 days. Water was added, and the resultant mixture was extracted with ethyl acetate. The organic extract was washed with brine, dried over magnesium sulphate and concentrated under reduced pressure. The concentrate was chromatographied on silica gel eluting with a mixture of methanol and ethyl acetate (1:19 v/v) to afford the two title products: 7-(3-acetamidophenyl)-5-hydroxymethyl-1-phenylbenzimidazole (0.38 g, 42%) m/z, 358.2 (M+H)+, and 7-(3-ethylaminophenyl)-5-hydroxymethyl-1-phenylbenzimidazole (0.20 g, 23%) m/z, 344.2 (M+H)$^+$.

Example 44

7-(3-Dimethylaminophenyl)-5-trifluoromethyl-1-phenylbenzimidazole and 7-(3-Methylaminophenyl)-5-trifluoromethyl-1-phenylbenzimidazole To a solution of 7-(3-aminophenyl)-5-trifluoromethyl-1-phenylbenzimidazole (1.0 g, 2.8 mmol) in tetrahydrofurane (5 ml) was added iodomethane (1.6 ml, 25.7 mmol) and triethylamine (2.3 ml, 16.6 mmol) and the resultant mixture was stirred at 40° C. overnight, whereafter it was partitioned between ethyl acetate and brine. The organic phase was dried over magnesium sulphate and concentrated under reduced pressure. The concentrate was chromatographied on silica gel eluting with a mixture of ethyl acetate and petroleum ether (1:1 v/v). Removal of solvent from the appropriate eluate fractions afforded 7-(3-dimethylaminophenyl)-5-trifluoromethyl-1-phenylbenzimidazole (83 mg, 8%) m/z, 382.2 (M+H)$^+$, and 7-(3-methylaminophenyl)-5-trifluoromethyl-1-phenylbenzimidazole (26 mg, 3%) m/z, 368.1 (M+H)$^+$.

Example 45

1-Phenyl-7-(3-((4-methylpiperazin-1-yl)methyl)phenyl)-5-trifluoromethylbenzimidazole To a suspension of 7-(3-(hydroxymethyl)phenyl)-1-phenyl-5-trifluoromethylbenzimidazole (6.0 g, 16.3 mmol) in anhydrous toluene (60 ml) was added thionyl chloride (1.43 ml, 19.5 mmol) and the mixture was stirred at ambient temperature for 30 min. The solvent was removed by evaporation under reduced pressure, and 7-(3-(chloromethyl)phenyl-phenyl-5-trifluoromethylbenzimidazole precipitated from the residue upon trituration with ethyl acetate, 5.65 g (90%).

To a cooled (0° C.) solution of the above product (0.97 g, 2.5 mmol) in NMP (5 ml) was added 1-methylpiperazine (0.84 ml, 7.5 mmol) and the resultant mixture was stirred at ambient temperature overnight and then partitioned between ethyl acetate and water. The organic layer was washed with aqueous calcium chloride (3M) and water, successively, dried over magnesium sulphate and evaporated under reduced pressure to afford the desired product, which precipitated upon trituration in a mixture of diethyl ether and petroleum ether (1:5, v/v), 0.2 g (18%), m/z, 451.2 (M+H)$^+$.

Example 46

7-(3-(1-Morpholinylmethyl)phenyl)-1-phenyl-5-trifluoromethylbenzimidazole

This was prepared analogeously to the above product from 7-(3-(chloromethyl)phenyl)-1-phenyl-5-trifluoromethylbenzimidazole (0.97 g, 2.5 mmol) and morpholine (0.74 ml, 7.5 mmol) in NMP (5 ml) to yield 0.81 g (74%), m/z, 382.1 (M+H)$^+$.

Example 47

7-(3-((Dimethylamino)methyl)Phenyl)-1-phenyl-5-trifluoromethylbenzimidazole

This was prepared analogeously to the above product from 7-(3-(chloromethyl)phenyl)-1-phenyl-5-trifluoromethylbenzimidazole (0.97 g, 2.5 mmol) and dimethyl amine (2 ml) in NMP (5 ml) to yield 0.54 g (55%), m/z, 396.2 (M+H)$^+$.

Example 48

5-Cyano-7-(4-(2-(4-morpholino)ethoxy)phenyl)-1-phenylbenzimidazole trifluoroacetic acid salt 5-Cyano-7-(4-hydroxyphenyl)-1-phenylbenzimidazole (62 mg, 0.2 mmol), 4-(2-hydroxyethyl)morpholine (39 mg, 0.3 mmol), diisopropyl azodicarboxylate (59 μl, 61 mg, 0.3 mmol), dichloromethane (2.0 ml), and resin-bound triphenylphosphine (360 mg, 0.3 mmol) were added sequentially to a tube and shaken at ambient temperature for 70 h. The liquid was filtered off and the resin washed twice with dichloromethane (2 ml) and twice with methanol (2 ml). The combined filtrates were evaporated and the residue was dissolved in dimethylsulphoxide (2 ml) and eluted through a prep LCMS column to give, after removal of the solvent, the desired product as a glass (15 mg, 14%) m/z, 425.5 (M+H)$^+$.

Example 49

7-(3-(N-Methyl acetamido)phenyl)-1-phenyl-5-trifluoromethylbenzimidazole

To a solution of 7-(3-acetamidophenyl)-1-phenyl-5-trifluoromethylbenzimidazole (0.35 g, 0.88 mmol) in anhydrous tetrahydrofurane (5 ml) was added sodium hydride (0.09 g 60% dispersion in mineral oil, 2.2 mmol). The resultant mixture was stirred for one hour at ambient temperature, whereafter iodomethane (0.44 ml, 7 mmol) was added and the temperature was raised to 40° C. for 30 min. The cooled mixture was partitioned between water and ethyl acetate. The organic layer was washed with water, dried over magnesium sulphate and concentrated under reduced pressure. The concentrate was eluted through silica gel with a mixture of dichloromethane and methanol (97:3, v/v). Removal of solvent from the eluate afforded the title product (0.13 g, 36%) m/z, 410.1 (M+H)$^+$.

Example 50

1-Phenyl-7-(4-pyridyl)-5-trifluoromethylbenzimidazole

A mixture of 7-iodo-1-phenyl-5-trifluoromethylbenzimidazole (3.0 g, 7.5 mmol), pyridine 4-boronic acid (1.38 g, 11.2 mmol), 1,3-propanediol (2.7 ml, 37.3 mmol), potassium carbonate (5.2 g, 37.3 mmol) and bis(triphenylphosphin)palladium dichloride (200 mg, 0.28 mmol) in a mixture of dimethoxyethane (30 ml) and water (15 ml) was stirred at reflux for 5 days. The cooled reaction mixture was concentrated under reduced pressure, and the concentrate was partitioned between water and ethyl acetate. The organic phase was dried and concentrated under reduced pressure, and the concentrate was purified by column chromatography on silica gel eluting with a mixture of ligroin and ethyl acetate (1:1 v/v). The product was isolated as a yellowish solid by evaporation of solvent from the eluate (1.55 g, 61%) m/z, 340.1 (M+H)$^+$.

Example 51

5-(Hydroxymethyl)-1-phenyl-7-(3-trifluoromethoxyphenyl)benzimidazole

A mixture of 5-ethoxycarbonyl-7-iodo-1-phenylbenzimidazole (6.5 g, 16.6 mmol), 3-trifluoromethoxyphenyl boronic acid (5.12 g, 24.9 mmol), 1,3-propanediol (6 ml, 82.9 mmol), potassium carbonate (11.4 g, 82.9 mmol) and bis(triphenylphosphin)palladium dichloride (100 mg, 0.14 mmol) in a mixture of dimethoxyethane (60 ml) and water (30 ml) was stirred at reflux for 30 minutes. The cooled reaction mixture was poured into water and the crude 5-ethoxycarbonyl-1-phenyl-7-(3-trifluoromethoxyphenyl)benzimidazole (6.6 g, 93%) was filtered off, washed with water and air-dried.

To a solution of this product (0.5 g, 1.17 mmol) in anhydrous THF (20 ml) was added lithium aluminum hydride (0.04 g, 1.17 mmol) and the resultant mixture was stirred in a nitrogen atmosphere at ambient temperature for 6 days. Aqueous sodium bicarbonate was added and the mixture was extracted with ethyl acetate. This extract was dried over magnesium sulphate, concentrated under reduced pressure and the concentrate was eluted through silica gel with ethyl acetate. The pure fractions were concentrated and the title product was isolated as the hydrochloride by addition of etheral hydrochloric acid to this concentrate (0.24 g, 49%) m/z, 385.1 (M+H)$^+$.

Example 52

7-(4-pyridyl N-oxide)-1-phenyl-5-trifluoromethylbenzimidazole

To a solution of 7-(4-pyridyl)-1-phenyl-5-trifluoromethylbenzimidazole (1.25 g, 3.69 mmol) in dichloromethane (50 ml) was added mCPBA (1.0 g, 5,9 mmol) and the resultant mixture was stirred at ambient temperature for 3 days. The solvent was removed by evaporation and the residue was partitioned between saturated, aqueous sodium carbonate and ethyl acetate. The organic layer was dried over magnesium sulphate and concentrated under reduced pressure. The concentrate was eluted through silica gel with a mixture of ethyl acetate and methanol (9:1, v/v) to afford the title product (1.15 g, 88%) m/z, 356.1 (M+H)$^+$.

Example 53

7-(3-chloro-4-pyridyl)-1-phenyl-5-trifluoromethylbenzimidazole

A solution of 7-(4-pyridyl N-oxide)-1-phenyl-5-trifluoromethylbenzimidazole (0.8 g, 2.25 mmol) in phosphoroxychloride (3 ml) was stirred at 80° C. for 3 hours. To the cooled solution was added saturated, aqueous sodium carbonate and the resultant mixture was extracted with ethyl acetate. The organic extract was dried over magnesium sulphate and concentrated under reduced pressure. The concentrate was purified by column chromatography on silica gel eluting with a mixture of ethyl acetate and ligroin (1:1, v/v). The title product was obtained as the hydrochloride by addition of etheral hydrochloric acid (2M) to the concentrated eluate (0.44 g, 48%) m/z, 374.1 (M+H)$^+$.

Example 54

7-(3-chloro-4-pyridyl-N-oxide)-1-phenyl-5-trifluoromethylbenzimidazole

This was prepared analogously to 7-(4-pyridyl N-oxide)-1-phenyl-5-trifluoromethylbenzimidazole from 7-(3-chloro-4-pyridyl)-1-phenyl-5-trifluoromethylbenzimidazole (0.45 g, 1.20 mmol) and mCPBA (0.74 g, 4.3 mmol) in dichloromethane (20 ml) to afford the title product (0.12 g, 26%) m/z, 390.1 (M+H)$^+$.

Example 55

7-(3-Acetylphenyl)-1-phenyl-5-trifluoromethylbenzimidazole

A mixture of 7-iodo-1-phenyl-5-trifluoromethylbenzimidazole (7.38 g, 19 mmol), 3-acetylphenyl boronic acid (4.67 g, 28.5 mmol), 1,3-propanediol (6.8 ml, 95 mmol), potassium carbonate (13.1 g, 95 mmol) and bis(triphenylphosphin)palladium dichloride (200 mg, 0.28 mmol) in a mixture of dimethoxyethane (60 ml) and water (30 ml) was stirred at reflux in a nitrogen atmosphere for 1 hour. The cooled reaction mixture was filtered through a pad of Celite and the filter was rinsed with ethyl acetate. The organic layer was collected, dried over magnesium sulphate and concentrated under reduced pressure. The title product precipitated upon addition of diethyl ether to the concentrate (6.17 g, 85%) m/z, 381.1 (M+H)$^+$.

Example 56

7-(3-Fluorophenyl)-1-Phenyl-5-trifluorophenylbenzimidazole

This was prepared analogeously to the above product from 7-iodo-1-phenyl-5-trifluoromethylbenzimidazole (0.78 g, 2 mmol) 3-fluorophenyl boronic acid (0.42 g, 3 mmol), 1,3-propanediol (0.72 ml, 10 mmol), potassium carbonate (1.38 g, 10 mmol) and bis(triphenylphosphin)palladium dichloride (50 mg, 0.07 mmol) in a mixture of dimethoxyethane (6.4 ml) and water (3.2 ml). The title product was crystallised from ligroin (0.61 g, 86%) m/z, 373.2 (M+H)$^+$.

Example 57

3-(3-Phenyl-6-trifluoromethyl-3H-benzimidazol-4-yl)acrylic acid methyl ester Methyl acrylate (2.7 ml, 30 mmol), 7-iodo-1-phenyl-5-trifluoromethylbenzimidazole (3.48 g, 10 mmol), triethylamine (2.79 ml, 20 mmol), palladium acetate (45 mg, 0.2 mmol), tri-o-tolylphosphine (161 mg, 0.53 mmol) and acetonitrile (50 ml) were combined and the mixture heated at reflux under an argon atmosphere for 17 h. The mixture was cooled, filtered through Dicalite and the filtrate was concentrated under reduced pressure. Crystals formed and were isolated by filtration and dried to give the title compound (3.2 g, 92%), m/z 347.0 (M+H)$^+$.

Example 58

3-(6-Cyano-3-phenyl-3H-benzimidazol-4-yl)acrylic acid methyl ester

Methyl acrylate (0.27 ml, 3 mmol), 5-cyano-7-iodo-1-phenylbenzimidazole (346 mg, 1.0 mmol), triethylamine (0.28 ml, 2 mmol) palladium acetate (4.5 mg, 0.02 mmol), tri-o-tolylphosphine (16.1 mg, 0.05 mmol) and acetonitrile (5 ml) were combined in Reactivial™. The mixture was heated under reflux under an argon atmosphere for 17 h. The mixture was cooled, filtered through Dicalite and the filtrate was concentrated under reduced pressure. Crystals formed and were isolated by filtration and dried to give the title compound (250 mg, 83%), m/z 304.2 (M+H)$^+$.

Example 59

7-(4-Morpholinyl)-1-phenyl-5-trifluoromethylbenzimidazole

A mixture of aniline (1.12 ml, 12.3 mmol) and 2,3-difluoro-1-nitro-5-trifluoromethylbenzene (2.8 g, 12.3 mmol) was heated at 110° C. for 24 h. Dichloromethane was added and the resulting precipitate filtered off. The filtrate was concentrated under reduced pressure then redissolved in ethyl acetate. 10% Palladium on carbon (0.5 g, Degussa) was added and the resulting suspension hydrogenated at 5 bar for 1 h. The reaction mixture was filtered through celite, washed with ethyl acetate and, the filtrate concentrated under reduced pressure. Formic acid (10 mL) was added and the mixture heated at 110° C. for 24 h. Concentration under reduced pressure gave 7-fluoro-1-phenyl-5-trifluoromethylbenzimidazole as a purple solid (3.0 g, 87%) m/z, 281.0 (M+H)$^+$.

To 7-fluoro-1-phenyl-5-trifluoromethylbenzimidazole (400 mg, 1.4 mmol) was added morpholine (1 ml, 1.1 mmol) and the mixture heated in a Personal Chemistry Smith Creator™ microwave for ten 30 minute periods at 245° C. The residue was chromatographed over silica gel to give the title compound as a solid (50 mg, 10%) m/z, 348.0 (M+H)$^+$.

Example 60

5-t-Butyl-7-(3-dimethylaminophenyl)-1-phenylbenzimidazole trifluoroacetic acid salt 5-t-Butyl-7-iodo-1-phenylbenzimidazole (94 mg, 0.25 mmol), toluene (1.5 ml), tetrakis(triphenylphosphine)palladium(0) (15 mg, 0.0125 mmol), 3-dimethylaminophenylboronic acid (41 mg, 0.25 mmol), ethanol (1.5 ml) and potassium carbonate (1M in water, 0.5 ml, 69 mg, 0.5 mmol) were added sequentially to a Smith Process Vial™ under nitrogen and irradiated for 70 s at 180° C. (150 W initial power) using a Personal Chemistry Smith Creator™ microwave. The tube was blown dry with nitrogen and the solid residue dissolved in dimethylsulphoxide (2 ml) and eluted through a prep LCMS column to give, after removal of the solvent, the desired product as a glass (102 mg, 42%) m/z, 370.5 (M+H)$^+$.

Example 61

7-(3-(1-Methoxyethyl)Phenyl)-1-phenyl-5-trifluoromethylbenzimidazole

To a stirred solution of 7-(3-(1-hydroxyethyl)phenyl)-1-phenyl-5-trifluoromethylbenzimidazole (0.9 g, 2.4 mmol) in anhydrous DMF (5 ml) was added sodium hydride (0.15 g 60% dispersion in mineral oil, 3.5 mmol) at ambient temperature. When the evolution of hydrogen had ceased iodomethane (0.25 ml, 2.6 mmol) was added and stirring was continued for 15 min. Four volumes of water was added and the resultant mixture was extracted with ethyl acetate. This extract was washed twice with aqueous calcium chloride (3M), dried over magnesium sulphate and evaporated under reduced pressure. The residue was eluted through silica gel with a mixture of ethyl acetate and petroleum ether (2:3, v/v). Trituration of the concentrated eluate in ligroin afforded the title product (0.35 g, 37%) m/z, 397.2 (M+H)$^+$.

Example 62

7-(1-Methyl-5-indolyl)-1-phenyl-5-trifluoromethylbenzimidazole

A mixture of 7-iodo-1-phenyl-5-trifluoromethylbenzimidazole (1.0 g, 2.5 mmol), 1-methyl-5-indolyl boronic acid (0.65 g, 3.73 mmol), 1,3-propanediol (0.9 ml, 12.4 mmol), potassium carbonate (1.71 g, 12.4 mmol) and bis(triphenylphosphin)palladium dichloride (100 mg, 0.14 mmol) in a mixture of dimethoxyethane (20 ml) and water (10 ml) was stirred at reflux in a nitrogen atmosphere for 1 hour. The cooled reaction mixture was partitioned between ethyl acetate and water and the organic layer was dried over magnesium sulphate and evaporated under reduced pressure. The residue was triturated in ethanol to afford the title product as an off-white solid (0.82 g, 84%) m/z, 392.1 (M+H)+.

Example 63

7-(3-(1-Hydroxyethyl)phenyl)-1-phenyl-5-trifluoromethylbenzimidazole

To a suspension of 7-(3-acetylphenyl)-1-phenyl-5-trifluoromethylbenzimidazole (0.95 g, 2.5 mmol) in ethanol (10 ml) was added sodium borohydride (0.1 g, 2.6 mmol) and the resultant mixture was stirred at 60° C. for 20 min. The cooled reaction mixture was concentrated under reduced pressure and the concentrate was partitioned between ethyl acetate and water. The organic layer was dried over magnesium sulphate and concentrated to a small volume (1-2 ml) under reduced pressure. The title product precipitated upon addition of ligroin to the concentrate (0.65 g, 68%) m/z, 383.1 (M+H)+.

Example 64

7-(3-Furyl)-1-phenyl-5-trifluoromethylbenzimidazole

A mixture of 7-iodo-1-phenyl-5-trifluoromethylbenzimidazole (0.5 g, 1.25 mmol), 3-furane boronic acid (0.2 g, 1.87 mmol), 1,3-propanediol (0.45 ml, 6.2 mmol), potassium carbonate (0.86 g, 6.2 mmol) and bis(triphenylphosphin)palladium dichloride (50 mg, 0.07 mmol) in a mixture of dimethoxyethane (10 ml) and water (15 ml) was stirred at reflux in a nitrogen atmosphere for 30 min. The cooled reaction mixture was partitioned between ethyl acetate and water and the organic layer was dried over magnesium sulphate and evaporated under reduced pressure. The residue was triturated in diethyl ether to afford the title product as an off-white solid (0.22 g, 54%) m/z, 329.1 (M+H)+.

Example 65

N,N-Diethyl-3-(3-phenyl-6-trifluoromethyl-3H-benzimidazol-4-yl)acrylamide

This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzoimidazol-yl)prop-2-en-1-one. The oily residue was purified by flash chromatography over silica gel (eluted with dichloromethane/methanol 0.5-2.5% gradient) to afford the title compound as a white solid (300 mg, 53%), m/z 388.0 (M+H)+.

Example 66

1-(4-Methylpiperazin-1-yl)-3-(3-phenyl-6-trifluoromethyl-3H-benzimidazol-4-yl)prop-2-en-1-one To a stirred suspension of aluminium trichloride (1.46 mmol, 195 mg) in dichloromethane (3 ml) was added dropwise N-methylpiperazine (1.83 mmol, 203 1). The resultant mixture was stirred for 0.5 h and to this, a solution of 3-(3-phenyl-6-trifluoromethyl-3H-benzimidazol-4-yl)acrylic acid methyl ester (0.73 mmol, 250 mg) was added dropwise. The resultant mixture stirred for 16 h at 60° C. Upon cooling, aqueous sodium carbonate (5%, 5 ml) was added and the mixture was shaken. The organic layer was isolated by filtration through a hydrophobic frit and evaporated under reduced pressure to give an off-white solid. Recrystallisation from diethyl ether afforded the title compound as a white powder (160 mg, 53%), m/z 415.2 (M+H)+.

Example 67

3-(3-Phenyl-6-trifluoromethyl-3H-benzimidazol-4-yl-1-piperidinylprop-2-en-1-one

This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one to afford the title compound as a white solid (150 mg, 51%), m/z 400.0 (M+H)+.

Example 68

1-(4-Morpholinyl)-3-(3-phenyl-6-trifluoromethyl-3H-benzimidazol-4-yl)Prop-2-en-1-one This was prepared from 3-(3-phenyl-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one to afford the title compound as a white solid (350 mg, 60%), m/z 402.2 (M+H)+.

Example 69

1-(4-Methyl-[1,4]-hexahydrodiazepin-1-yl)-3-(3-phenyl-6-trifluoromethyl-3H-benzimidazol-4-yl)prop-2-en-1-one This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzoimidazol-4-yl)prop-2-en-1-one to afford the title compound as a white solid (80 mg, 26%), m/z 429.2 (M+H)+.

Example 70

N-(2-Cyanoethyl)-3-(3-phenyl-6-trifluoromethyl-3H-benzimidazol-4-yl)acrylamide

This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford, after removal of the solvent, the title compound as a white solid (13 mg, 5%), m/z 385.0 (M+H)+.

Example 71

3-(3-Phenyl-6-trifluoromethyl-3H-benzimidazol-4-yl)-N-propylacrylamide

This was prepared from 3-(3-phenyl-6-trifluoromethyl-3H-benzoimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily

Example 72

N-(2-Dimethylaminoethyl)-3-(3-phenyl-6-trifluoromethyl-3H-benzimidazol-4-yl)acrylamide This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by flash chromatography over silica gel (eluted with dichloromethane/methanol 2-5% gradient) to afford the title compound as a white solid (29 mg, 5%), m/z 403.4 $(M+H)^+$.

Example 73

3-(3-Phenyl-6-trifluoromethyl-3H-benzimidazol-4-yl)-1-(4-trifluoromethyl-piperidin-1-yl)prop-2-en-1-one This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford, after removal of the solvent, the title compound as a white solid (40 mg, 12%), m/z 468.2 $(M+H)^+$.

Example 74

7-(3-(2-Hydroxy-2-propyl)phenyl)-1-phenyl-5-trifluoromethylbenzimidazole

To an ice-cooled solution of 7-(3-acetylphenyl)-1-phenyl-5-trifluoromethylbenzimidazole ((0.76 g, 2.0 mmol) in anhydrous tetrahydrofurane (5 ml) was added a solution of methylmagnesium bromide (1.0 ml, 3M) dropwise over 5 min. The ice-bath was removed and the mixture was stirred at ambient temperature for 4 hours. Aqueous ammonium chloride, and subsequently ethyl acetate, was added.

The organic layer was dried over magnesium sulphate and evaporated under reduced pressure. The residue was purified by column chromatography eluting with a mixture of petroleum ether and ethyl acetate (1:1, v/v) to afford the title product (0.26 g, 33%) m/z, 397.2 $(M+H)^+$.

Example 75

7-(4-Hydroxypiperidinyl)-1-phenyl-5-trifluoromethylbenzimidazole

To 7-fluoro-1-phenyl-5-trifluoromethylbenzimidazole (500 mg, 1.78 mmol) was added piperidine (2 g, 23 mmol) and the mixture heated in a Personal Chemistry Smith Creator™ microwave for two 30 minute periods at 245° C. The residue was chromatographed over silica gel to give the title compound as a solid (350 mg, 54%) m/z, 362.2 $(M+H)^+$.

Example 76

7-(3-Fluorophenyl)-5-methyl-1-Phenylbenzimidazole trifluoroacetic acid salt

This was prepared in a similar manner to 5-t-butyl-7-(3-dimethylaminophenyl)-1-phenylbenzimidazole, using 7-iodo-5-methyl-1-phenylbenzimidazole (84 mg, 0.25 mmol) to realise the desired product (57 mg, 27%) m/z, 303.3 $(M+H)^+$.

Example 77

7-(4-Hydroxybut-1-ynyl)-1-phenyl-5-trifluoromethylbenzimidazole

To a stirred solution of 7-iodo-1-phenyl-5-trifluoromethylbenzimidazole (9.7 g, 25 mmol) and tetrakis(triphenylphosphine)palladium(0) (2.9 g, 5 mmol) in pyrrolidine (75 ml) was added a solution of 3-butyn-1-ol (7.0 g, 0.1 mol) in pyrrolidine (75 ml), then copper (I) iodide (475 mg, 2.5 mmol). The resulting solution was heated to 75° C. with stirring under nitrogen. After 2.5 h the reaction mixture was allowed to cool, treated with saturated aqueous ammonium chloride and extracted with diethyl ether. The combined organic extracts were dried over anhydrous sodium sulphate and the solvent removed under reduced pressure to leave a residue (13.6 g). This residue was flash chromatographed over silica gel (eluted with dichloromethane/diethyl ether 4:1) to give the desired product (3.95 g, 48%) m/z, 330.8 $(M+H)^+$.

Example 78

7-(1-(1-(4-Hydroxyethylpiperazinyl)ethyl)-1-methylamino)-1-phenyl-5-trifluoromethylbenzimidazole trifluoroacetic acid salt To 7-fluoro-1-phenyl-5-trifluoromethylbenzimidazole (2.4 g, 8.6 mmol) was added N-methylethanolamine (9.6 ml, 12 mmol) and the mixture heated (in batches) in a Personal Chemistry Smith Creator™ microwave for four 30 minute periods at 245° C. The reaction mixture was partitioned between dichloromethane and water. The organic layer was separated, dried and concentrated under reduced pressure. The residue was chromatographed over silica gel to give 7-[1-(hydroxyethyl)-1-methylamino]-1-phenyl-5-trifluoromethylbenzimidazole as a solid (1.2 g, 42%) m/z, 336.0 $(M+H)^+$.

To a solution of 7-[1-(hydroxyethyl)-1-methylamino]-1-phenyl-5-trifluoromethylbenzimidazole (1.2 g, 3.6 mmol) in dichloromethane at 0° C. was added triethylamine (0.5 ml, 3.6 mmol) then methanesulphonyl chloride (0.28 ml, 3.6 mmol). The reaction mixture was stirred at 0° C. for 2 h then allowed to warm to room temp and stirred for a further 20 h. The resulting residue was chromatographed over silica gel to give 7-[1-(2-methylsulphonylhydroxy)ethyl-1-methylamino]-1-phenyl-5-trifluoromethylbenzimidazole as a solid (1.0 g, 67%).

To a solution of 7-[1-(2-methylsulphonylhydroxy)ethyl-1-methylamino]-1-phenyl-5-trifluoromethylbenzimidazole (28 mg, 0.067 mmol) in dimethylsulphoxide (0.4 ml) at 0° C. was added N-methylpiperazine (0.1 ml, 0.9 mmol). The reaction was stirred at 70° C. for 18 h then allowed to warm to room temp and stirred for a further 20 h. Purification by prep LCMS gave the title compound as a gum (5.6 mg, 18%) m/z, 448.0 $(M+H)^+$.

Example 79

7-(1-(1-(4-Methylpiperazinyl)ethyl)-1-methyl)amino-1-phenyl-5-trifluoromethylbenzimidazole trifluoroacetic acid salt To a solution of 7-[1-(2-methylsulphonylhydroxy)ethyl-1-methylamino]-1-phenyl-5-trifluoromethylbenzimidazole (28 mg, 0.067 mmol) in dimethylsulphoxide (0.4 ml) at 0° C. was added N-methylpiperazine (0.1 ml). The reaction was stirred at 70° C. for 18 h then allowed to warm to room temp and stirred for a further 20 h. Purification by prep LCMS gave the title compound as a gum (9.9 mg, 35%) m/z, 418.0 (M+H)$^+$.

Example 80

7-(3-(4-Morpholino)prop-1-ynyl)-1-phenyl-5-trifluoromethylbenzimidazole trifluoroacetic acid salt 7-(3-Hydroxyprop-1-ynyl)1-phenyl-5-trifluoromethylbenzimidazole (32 mg, 0.1 mmol), toluene (0.6 ml), and diisopropylethylamine (52 µl, 39 mg, 0.3 mmol) were added sequentially to a Smith Process Vial™, cooled to −15° C. and methanesulphonyl chloride (9 µl, 13 mg, 0.11 mmol) added. The mixture was stirred for 0.5 h as it warmed to ambient temperature then stirred for 1.5 h. The mixture was then cooled to −15° C. and morpholine (11 µl, 11 mg, 0.12 mmol) added. This mixture was stirred for 0.5 h as it warmed to ambient temperature then stirred for 0.5 h. The mixture was then irradiated for 1800 s at 200° C. (300 W initial power) using a Personal Chemistry Smith Creator™ microwave. The tube was blown dry with nitrogen and the solid residue dissolved in dimethylsulphoxide (2 ml) and eluted through a prep LCMS column to give, after removal of the solvent, the desired product as a glass (61 mg, 60%) m/z, 386.1 (M+H)$^+$.

Example 81

N,N-Diethyl-3-(3-Phenyl-6-trifluoromethyl-3H-benzimidazol-4-yl)propionamide

Alumina supported formate was prepared according to the procedure of Danks and Desai (T. N. Danks and B. Desai, *Green Chemistry*, 2002, 4, 179-180). A Smith Process Vial™ was loaded with alumina supported formate (0.5 g), Wilkinson's catalyst (0.5 mg), N,N-diethyl-3-(3-phenyl-6-trifluoromethyl-3H-benzimidazol-4-yl)acrylamide (0.064 mmol, 25 mg) and dimethylsulphoxide (0.5 ml) and was irradiated for 600 s at 180° C. using a Personal Chemistry Smith Creator™ microwave. The mixture was filtered to remove the solid support and the filtrate was purified by LCMS to give, after evaporation, the title compound as a solid (7.8 mg, 31%), m/z 390.0 (M+H)$^+$.

Example 82

3-(6-tert-Butyl-3-phenyl-3H-benzimidazol-4-yl)-1-(piperidin-1-yl)prop-2-en-1-one 5-t-Butyl-7-iodo-1-phenylbenzimidazole was prepared in a similar manner to 5-cyano-7-iodo-1-phenylbenzimidazole, using 4-t-butyl-2,6-dinitrophenol as starting material to realise the desired product (11.75 g, 44%) m/z, 377.2 (M+H)$^+$.
The title compound was prepared in a similar manner to 1-(4-methylpiperazin-1-yl)-3-(3-phenyl-6-trifluoromethyl-3H-benzimidazol-4-yl)prop-2-en-1-one using 5-t-butyl-7-iodo-1-phenylbenzimidazole as starting material. The oily residue was purified by preparative LCMS to afford the title compound as a white solid (25 mg, 22%), m/z 388.2 (M+H)$^+$.

Example 83

N-Ethyl-N-isopropyl-3-(3-phenyl-6-trifluoromethyl-3H-benzimidazol-4-yl)acrylamide This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford the title compound as a white solid (7.2 mg, 6%), m/z 402.0 (M+H)$^+$.

Example 84

N-(1-Methylpiperidin-4-yl)methyl-3-(3-phenyl-6-trifluoromethyl-3H-benzimidazol-4-yl)acrylamide trifluoroacetic acid salt This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford the title compound as a white solid (32 mg, 25%), m/z 443.0 (M+H)$^+$.

Example 85

N-Methyl-N-(1-methylpyrrolidin-3-yl)-3-(3-phenyl-6-trifluoromethyl-3H-benzimidazol-4-yl)acrylamide trifluoroacetic acid salt This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford the title compound as a white solid (11.4 mg, 9%), m/z 429.0 (M+H)$^+$.

Example 86

3-(6-tert-Butyl-3-phenyl-3H-benzimidazol-4-yl)-N-methyl-N-(1-methylpiperidin-4-yl)acrylamide trifluoroacetic acid salt This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford the title compound as a white solid (15.3 mg, 12%), m/z 431.0 (M+H)$^+$.

Example 87

7-(4-(Diethylaminobutyl)-1-phenyl-5-trifluoromethylbenzimidazole trifluoroacetic acid salt 7-(4-Hydroxybutynyl-phenyl-5-trifluoromethylbenzimidazole (1 g, 3.03 mmol), was dissolved in ethyl acetate (20 ml) and a catalytic amount of Degussa catalyst (palladium, 10 wt. % (dry basis) on activated carbon, containing 50% water) was added. This was treated with hydrogen gas in a Buchi hydrogenator at 5 bar pressure for 18 h. The reaction mixture was filtered through celite and evaporated to dryness giving 7-(4-hydroxy)butyl-1-phenyl-5-trifluoromethylbenzimidazole a yellow oil which crystallised on standing.
7-(4-Hydroxy)butyl-1-phenyl-5-trifluoromethylbenzimidazole (900 mg, 2.7 mmol) was dissolved in dichloromethane (20 ml) and triethylamine (1.13 ml, 8.1 mmol), cooled to 0° C. Methanesulphonyl chloride (0.3 ml, 2.97 mmol), was added and stirred at 0° C. for 3 h. The solvent was removed under reduced pressure and the resulting solid was triturated with ethyl acetate and filtered. The filtrate was evaporated under reduced pressure giving the mesylate as a yellow oil.

The mesylate (70 mg, 0.17 mmol) was dissolved in ethanol (2 ml) and diethylamine (0.1 ml, 9.7×10$^{-4}$ mol) added. The resulting solution was heated to 60° C. with shaking for 66 h. The reaction mixture was purified by prep HPLC (acetonitrile/water/trifluoroacetic acid) to give the title compound (15.9 mg, 19%) m/z, 390.0 (M+H)$^+$.

Example 88

7-(4-((N-(2-Cyanoethyl)-N-methyl)amino)-1-butyl)-1-phenyl-5-trifluoromethylbenzimidazole trifluoroacetic acid salt This was prepared in a similar manner to 7-(4-(diethylamino)butyl)-1-phenyl-5-trifluoromethylbenzimidazole trifluoroacetic acid salt using 3-methylaminopropionitrile (0.1 ml, 1.07 mmol) to realise the desired product (3.5 mg, 4%) m/z, 401.2 (M+H)$^+$.

Example 89

3-(3-phenyl-6-trifluoromethyl-3H-benzimidazol-4-yl)-1-(pyrollidin-1-yl)prop-2-en-1-one This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford the title compound as a white solid (7.3 mg, 7%), m/z 386.0 (M+H)$^+$.

Example 90

1-(2.5-Dihydropyrrol-1-yl)-3-(3-phenyl-6-trifluoromethyl-3H-benzimidazol-4-yl)prop-2-en-1-one This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford the title compound as a white solid (6.2 mg, 6%), m/z 384.0 (M+H)$^+$.

Example 91

N-(2-Cyanoethyl)-N-methyl-3-(3-phenyl-6-trifluoromethyl-3H-benzimidazol-4-yl)acrylamide This was prepared from 3-(3-phenyl-6-trifluoromethyl-3H-benzimidazol-4-yl)acrylic acid methyl ester in a similar manner to 1-(4-methylpiperazin-1-yl)-3-(3-phenyl-6-trifluoromethyl-3H-benzimidazol-4-yl)prop-2-en-1-one. The oily residue was purified by preparative LCMS to afford the title compound as a white solid (5.6 mg, 5%), m/z 399.0 (M+H)$^+$.

Example 92

1-Phenyl-7-(3-(1-(1,2,3,6-tetrahydropyridinyl))prop-1-ynyl)-5-trifluoromethylbenzimidazole This was prepared in a similar manner to 7-(3-(4-morpholinyl)prop-1-ynyl)-1-phenyl-5-trifluoromethylbenzimidazole using 1,2,3,6-tetrahydropyridine in place of morpholine to realise the desired product (18 mg, 24%) m/z, 382.4 (M+H)$^+$.

Example 93

1-Phenyl-7-(3-(1-piperidinyl)prop-1-ynyl)-5-trifluoromethylbenzimidazole

This was prepared in a similar manner to 7-(3-(4-morpholinyl)prop-1-ynyl)-1-phenyl-5-trifluoromethylbenzimidazole using piperidine in place of morpholine to realise the desired product (13 mg, 17%) m/z, 384.4 (M+H)$^+$.

Example 94

7-[1-(3-Dimethylamino)pyrrolidinyl]-1-phenyl-5-trifluoromethylbenzimidazole trifluoroacetic acid salt 7-Fluoro-1-phenyl-5-trifluoromethylbenzimidazole (300 mg, 1.07 mmol) and 3-(dimethylamino)pyrrolidine (1.7 g, 15 mmol) were heated in a Personal Chemistry Smith Creator™ microwave for three 30 minute periods at 245° C. The reaction mixture was partitioned between dichloromethane and water. The organic layer was separated, dried and concentrated under reduced pressure. Purification by prep LCMS gave the title compound as a solid (150 mg) m/z, 374.8 (M+H)$^+$.

Intermediates

7-Amino-5-cyano-1-phenylbenzimidazole

To a cooled (5° C.) solution of 4-chloro-3,5-dinitrobenzonitril (50 g, 0.22 mol) in anhydrous DMF (200 ml) was added aniline (40 ml, 0.44 mol) dropwise over 1 hour. The resultant mixture was stirred for additionally 1 hour at 0° C. and then poured into ice-water (1400 g). The precipitate was filtered off, washed with water and air-dried to afford N-phenyl-4-cyano-2,6-dinitroaniline, quantitatively.

To a stirred suspension of N-phenyl- 4-cyano-2,6-dinitroaniline (16.4 g, 57.8 mmol) and SnCl$_2$, 2H$_2$O (130.5 g, 0.58 mol) in abs. ethanol (300 ml) was added formic acid (90 ml) dropwise at ambient temperature. The reaction is exothermic. The reaction was allowed to proceed at ambient conditions overnight. The resultant mixture was rendered alkaline by addition of saturated, aqueous sodium carbonate and was filtered through Celite. The filtrate was extracted with dichloromethane. The organic extract was dried over magnesium sulphate and evaporated under reduced pressure. The residue was triturated in cold ethyl acetate to leave the title product (8.65 g, 64%).

7-Amino-1-phenyl-5-trifluoromethylbenzimidazole

This was prepared in analogy with 7-amino-5-cyano-1-phenylbenzimidazole using 4-chloro-3,5-dinitrobenzotrifluoride as the starting material (11 g, 75%)

5-Cyano-7-iodo-1-phenylbenzimidazole

A suspension of 7-Amino-5-cyano-1-phenylbenzimidazole (12.5 g, 53.4 mmol) in hydrochloric acid (90 ml, 25% w/v) was diazotised with a solution of sodium nitrite (3.7 g, 53.4 mmol) in water (20 ml). The resultant mixture was stirred for 30 min at 0° C. whereafter a solution of potassium iodide (14.2 g, 85.5 mmol) in water (40 ml) was added dropwise. Stirring was continued for 10 min at 0° C., and then the temperature was raised to 80° C. for 30 min. After cooling, aqueous sodium sulphite (1M) was added and the resultant mixture was extracted with dichloromethane. Column chromatographic work-up of the dried and concentrated organic extract afforded the title product (6.5 g, 35%)

7-iodo-1-phenyl-5-trifluoromethylbenzimidazole

This was prepared analogously to 5-cyano-7-iodo-1-phenylbenzimidazole from 4-chloro-3,5-dinitrobenzotrifluoride (6.8 g, 67%)

5-Ethoxycarbonyl-7-iodo-1-phenylbenzimidazole

This was prepared analogously to 5-cyano-7-iodo-1-phenylbenzimidazole from ethyl 4-chloro-3,5-dinitrobenzoate (0.7 g, 50%)

5-t-Butyl-7-iodo-1-phenylbenzimidazole

This was prepared in a similar manner to 5-cyano-7-iodo-1-phenylbenzimidazole, using 4-t-butyl-2,6-dinitrophenol as starting material to realise the desired product (11.75 g, 44%) m/z, 377.2 (M+H)$^+$.

7-iodo-5-methyl-1-phenylbenzimidazole

This was prepared in a similar manner to 5-cyano-7-iodo-1-phenylbenzimidazole, using 4-methyl-2,6-dinitrophenol as starting material to realise the desired product (1.45 g, 16%) m/z, 335.1 (M+H)$^+$.

7-(3-Hydroxyprop-1-ynyl)-1-phenyl-5-trifluoromethylbenzimidazole

To a stirred solution of 7-iodo-1-phenyl-5-trifluoromethylbenzimidazole (9.7 g, 25 mmol) and tetrakis (triphenylphosphine)palladium(0) (2.9 g, 5 mmol) in pyrrolidine (75 ml) was added a solution of 2-propyn-1-ol (5.6 g, 0.1 mol) in pyrrolidine (75 ml), then copper (I) iodide (475 mg, 2.5 mmol). The resulting solution was heated to 75° C. with stirring under nitrogen. After 5 h the reaction mixture was allowed to cool, treated with saturated aqueous ammonium chloride and extracted with diethyl ether. The combined organic extracts were dried over anhydrous sodium sulphate and the solvent removed under reduced pressure to leave a residue (14.5 g). This residue was flash chromatographed over silica gel (eluted with dichloromethane/diethyl ether 4:1) to give the desired product (2.53 g, 32%) m/z, 316.8 (M+H)$^+$.

Test Methods

Test Method 1

In vitro Inhibition of $^3$H-flunitrazepam ($^3$H-FNM) Binding

The GABA recognition site and the benzodiazepine modulatory unit can selectively be labelled with $^3$H-flunitrazepam.

Tissue Preparation

Preparations are performed at 0-4° C. unless otherwise indicated. Cerebral cortex from male Wistar rats (150-200 g) is homogenised for 5-10 sec in 20 ml Tris-20 HCl (30 mM, pH 7.4) using an Ultra-Turrax homogeniser. The suspension is centrifuged at 27,000×g for 15 min and the pellet is washed three times with buffer (centrifuged at 27,000×g for 10 min). The washed pellet is homogenized in 20 ml of buffer and incubated on a water bath (37° C.) for 30 min to remove endogenous GABA and then centrifuged for 10 min at 27,000×g. The pellet is then homogenized in buffer and centrifuged for 10 min at 27,000×g. The final pellet is resuspended in 30 ml buffer and the preparation is frozen and stored at −20° C.

Assay

The membrane preparation is thawed and centrifuged at 2° C. for 10 min at 27,000×g. The pellet is washed twice with 20 ml 50 mM Tris-citrate, pH 7.1 using an Ultra-Turrax homogeniser and centrifuged for 10 min at 27,000×g. The final pellet is resuspended in 50 mM Tris-citrate, pH 7.1 (500 ml buffer per g of original tissue), and then used for binding assays. Aliquots of 0.5 ml tissue are added to 25 μl of test solution and 25 μl of $^3$H-FNM (1 nM, final concentration), mixed and incubated for 40 min at 2° C. Non-specific binding is determined using Clonazepam (1 μM, final concentration). After incubation the samples are added 5 ml of ice-cold buffer and poured directly onto Whatman GF/C glass fibre filters under suction and immediately washed with 5 ml ice-cold buffer. The amount of radioactivity on the filters is determined by conventional liquid scintillation counting. Specific binding is total binding minus non-specific binding.

Results 25-75% inhibition of specific binding must be obtained, before calculation of an IC$_{50}$.

The test value will be given as IC$_{50}$ (the concentration (μM) of the test substance which inhibits the specific binding of $^3$H-FNM by 50%).

$$IC_{50} = \text{(applied test substance concentration, μM)} \times \frac{1}{\left(\frac{C_o}{C_x} - 1\right)}$$

where $C_o$ is specific binding in control assays, and $C_x$ is the specific binding in the test assay.

(The calculations assume normal mass-action kinetics).

Test results from these experiments with a number of compounds of the invention are shown in Table 1 below.

TABLE 1

| Test compound Compound of Example: | In vitro binding IC$_{50}$ (μM) |
|---|---|
| 6 | 0.0042 |
| 10 | 0.018 |
| 12 | 0.030 |
| 23 | 0.038 |
| 33 | 0.019 |
| 41 | 0.027 |
| 51 | 0.012 |
| 57 | 0.046 |
| 65 | 0.020 |
| 75 | 0.042 |
| 80 | 0.18 |
| 81 | 0.038 |
| 88 | 0.10 |
| 92 | 0.048 |
| 94 | 0.090 |

The invention claimed is:

1. A compound of general formula (I):

(I)

or an N-oxide thereof, or any of its isomers or any mixture of its isomers, or a pharmaceutically acceptable salt thereof, wherein R⁵ is halo, trifluoromethyl, trifluoromethoxy, cyano, nitro, alkyl, alkoxy, -alkyl-OR$^a$, —CH=N—O—R$^a$ or —(C=O)—O-alkyl; wherein R$^a$ is hydrogen or alkyl;

R⁷ is

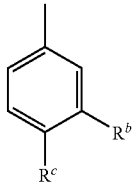

wherein one of R$^b$ and R$^c$ is hydrogen; and the other of R$^b$ and R$^c$ is hydrogen, halo, cyano, hydroxy, nitro, trifluoromethyl, trifluoromethoxy, alkyl, alkoxy, alkylcarbonyl or —NR$^d$—(C=O)—R$^e$; wherein the alkyl and alkoxy are optionally substituted with one or more substituents selected from the group consisting of: hydroxy, alkoxy, halo, and —NR'R"; R$^d$ and R$^e$ independently of each other are selected from hydrogen and alkyl; R' and R" independently of each other are selected from hydrogen and alkyl;

—NR$^f$R$^g$, -alkyl-NR$^f$R$^g$, —(C=O)—NR$^f$R$^g$, —O—NR$^f$R$^g$; —O-alkyl-NR$^f$R$^g$; —NR$^h$-alkyl-NR$^f$R$^g$; wherein R$^h$ is hydrogen or alkyl; R$^f$ and R$^g$ independently of each other are hydrogen or alkyl; or R$^f$ and R$^g$ together with the nitrogen to which they are attached form a 5- to 7-membered heterocyclic ring, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxyalkyl, or —NR'R";

wherein R' and R" independently of each other are hydrogen or alkyl; or R$^b$ and R$^c$ together represent —O—CH$_2$—O—; or R⁷ is —NR$^h$—(C=O)—R$^i$, —N=CH—R$^i$, or —C≡C—R$^i$; wherein R$^h$ is hydrogen or alkyl; and R$^i$ is alkyl or phenyl, which alkyl or phenyl is optionally substituted with hydroxy, trifluoromethyl, cyano or alkyl; or —NR$^j$R$^k$, -alkyl-NR$^j$R$^k$, —CH=CH—(C=O)—NR$^j$R$^k$, —CH=CH—(C=O)—O-alkyl, -alkyl-(C=O)—NR$^j$R$^k$, or —C≡C—CH$_2$—NR$^j$R$^k$; wherein R$^j$ and R$^k$ independently of each other are selected from the group consisting of hydrogen, alkyl, -alkyl-CN, -alkyl-R'R" and -alkyl-R$^l$;

wherein R' and R" independently of each other are hydrogen or alkyl; R$^l$ is a 5- to 7-membered heterocyclic ring comprising one nitrogen atom, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxyalkyl, or —NR'R"; wherein R' and R" independently of each other are hydrogen or alkyl;

or R⁷ is a heteroaryl group which heteroaryl group is optionally substituted with one or more substituents independently selected from the group consisting of: halo, trifluoromethyl, trifluoromethoxy, cyano, nitro, alkyl, and alkoxy;

with the proviso that the compound is not
7-(3-Aminophenyl)-1-phenyl-5-trifluoromethylbenzimidazole,
7-(3-Pyridyl)-1-phenyl-5-trifluoromethylbenzimidazole,
1,7-Diphenyl-5-trifluoromethylbenzimidazole,
7-benzoylamino-1-phenyl-5-trifluoromethylbenzimidazole, or
7-amino-1-phenyl-5-trifluoromethylbenzimidazole.

2. The compound of claim 1, or an N-oxide thereof, or any of its isomers or any mixture of its isomers, or a pharmaceutically acceptable salt thereof, wherein R⁵ is selected from the group of methyl, tertbutyl, trifluoromethyl, hydroxymethyl, cyano, ethoxycarbonyl, —CH=N—OH, and —CH=N—O—CH$_3$.

3. The compound of claim 1, or an N-oxide thereof, or any of its isomers or any mixture of its isomers, or a pharmaceutically acceptable salt thereof, wherein R⁷ is

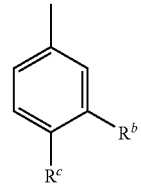

wherein one of R$^b$ and R$^c$ is hydrogen; and the other of R$^b$ and R$^c$ is hydrogen, halo, cyano, hydroxy, nitro, trifluoromethyl, trifluoromethoxy, alkyl, alkoxy, alkylcarbonyl or —NR$^d$—(C=O)—R$^e$; wherein the alkyl and alkoxy are optionally substituted with one or more substituents selected from the group consisting of: hydroxy, alkoxy, halo, and —NR'R";

—NR$^f$R$^g$, -alkyl-NR$^f$R$^g$, —(C=O)—NR$^f$R$^g$, —O—NR$^f$R$^g$; —O-alkyl-NR$^f$R$^g$; —NR$^h$-alkyl -NR$^f$R$^g$; wherein R$^d$, R$^e$, R$^f$, R$^g$, R$^h$, R' and R" are as defined in claim 1.

4. The chemical compound of claim 1, or an N-oxide thereof, or any of its isomers or any mixture of its isomers, or a pharmaceutically acceptable salt thereof, wherein R⁷ is 3,4-methylenedioxyphenyl.

5. The chemical compound of claim 1, or an N-oxide thereof, or any of its isomers or any mixture of its isomers, or a pharmaceutically acceptable salt thereof, wherein R⁷ is R⁷ is
—NR$^h$—(C=O)—R$^i$, —N=CH—R$^i$, or —C≡C—R$^i$;
wherein R$^h$ is hydrogen or alkyl; and R$^i$ is alkyl or phenyl, which alkyl or phenyl is optionally substituted with hydroxy, trifluoromethyl, cyano or alkyl; or —NR$^j$R$^k$, -alkyl-NR$^j$R$^k$, —CH=CH—(C=O)—NR$^j$R$^k$, —CH=CH—(C=O)—O-alkyl, -alkyl-(C=O) —NR$^j$R$^k$, or —C≡C—CH$_2$—NR$^j$R$^k$; wherein R$^j$ and R$^k$ independently of each other are selected from the group consisting of hydrogen, alkyl, -alkyl-CN, -alkyl-R'R" and -alkyl-R$^l$; wherein R' and R" independently of each other are hydrogen or alkyl; R$^l$ is a 5- to 7-membered heterocyclic ring comprising one nitrogen atom, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxyalkyl, or —NR'R"; wherein R' and R" independently of each other are hydrogen or alkyl; or $R^j$ and $R^k$ together with the nitrogen to which they are attached form a 5- to 7-membered heterocyclic ring, which heterocyclic ring may optionally comprise as a ring member, one oxygen atom, and/or one additional nitrogen atom, and/or one carbon-carbon double bond, and/or one carbon-nitrogen bond; and which heterocyclic ring may optionally be substituted with trifluoromethyl, alkyl, hydroxy, hydroxyalkyl, or —NR'R"; wherein R' and R" independently of each other are hydrogen or alkyl.

6. The chemical compound of claim 1, wherein $R^7$ is indolyl, pyridyl, or furyl, optionally substituted with halo or methyl.

7. The compound of claim 1, which is 7-(3-Chlorophenyl)-1-phenyl-5-trifluoromethylbenzimidazole;
7-(3-Aminophenyl)-5-formyl-1-phenylbenzimidazole oxime;
O-Methyl 7-(3-Aminophenyl)-5-formyl-1-phenylbenzimidazole oxime;
7-(N-benzylideneamino)-1-phenyl-5-trifluoromethylbenzimidazole;
7-(N-(4-cyanobenzylidene)amino)-1-phenyl-5-trifluoromethylbenzimidazole;
7-(N-(3-cyanobenzylidene)amino)-1-phenyl-5-trifluoromethylbenzimidazole;
7-(3-Aminophenyl)-5-cyano-1-phenylbenzimidazole;
7-(3-(Hydroxymethyl)phenyl)-1-phenyl-5-trifluoromethylbenzimidazole;
1-Phenyl-7-(3-(1,2,3,6-tetrahydropyridine-1-ylmethyl)phenyl)-5-trifluoromethyl-benzimidazole;
7-(3-Acetamidophenyl)-5-ethoxycarbonyl-1-phenylbenzimidazole;
7-(3-Aminophenyl)-5-ethoxycarbonyl-1-phenylbenzimidazole;
5-(Ethoxycarbonyl)-7-(3-(hydroxymethyl)phenyl)-1-phenylbenzimidazole;
7-(3-Cyanophenyl)-1-phenyl-5-trifluorophenylbenzimidazole;
5-Cyano-7-(3-nitrophenyl)-1-phenylbenzimidazole;
5-Cyano-7-(3-hydroxymethylphenyl)-1-phenylbenzimidazole;
5-Cyano-7-(3-((1-methylpiperazin-4-yl)methyl)phenyl)-1-phenylbenzimidazole;
5-Cyano-7-(3-(diethylaminomethyl)phenyl)-1-phenyl-benzimidazole;
7-(3-Acetamidophenyl)-5-cyano-1-phenylbenzimidazole;
5-Cyano-7-(4-methoxyphenyl)-1-phenylbenzimidazole;
5-Cyano-7-(3-methoxyphenyl)-1-phenylbenzimidazole;
5-Cyano-7-(4-cyanophenyl)-1-phenylbenzimidazole;
5-Cyano-7-(3-fluorophenyl)-1-phenylbenzimidazole;
5-Cyano-7-(4-hydroxyphenyl)-1-phenylbenzimidazole;
5-Cyano-7-[3-(dimethylamino)phenyl]-1-phenylbenzimidazole;
5-Cyano-7-(3,4-methylenedioxyphenyl)-1-phenylbenzimidazole;
5-Cyano-7-(pyridin-4-yl)-1-phenylbenzimidazole;
7-(3-Aminophenyl)-5-hydroxymethyl-1-phenylbenzimidazole;
5-Ethoxycarbonyl-7-(3-((morpholin-4-yl)methyl)phenyl)-1-phenylbenzimidazole;
5-Ethoxycarbonyl-7-(3-((1-methylpiperazin-4-yl)methyl)phenyl)-1-phenylbenzimidazole;
5-Ethoxycarbonyl-7-(3-((dimethylamino)methyl)phenyl)-1-phenylbenzimidazole;
5-Cyano-7-(3-cyanophenyl)-1-phenylbenzimidazole;
5-Cyano-7-(4-nitrophenyl)-1-phenylbenzimidazole;
7-(4-Acetamidophenyl)-5-cyano-1-phenylbenzimidazole;
7-(3-Acetamidophenyl)-1-phenyl-5-trifluoromethylbenzimidazole;
O-Methyl 7-(3-acetmidophenyl)-5-formyl-1-phenylbenzimidazole oxime;
O-Methyl 7-(3-(dimethylamino)phenyl)-5-formyl-1-phenylbenzimidazole oxime;
5-Cyano-7-(4-diethylaminomethylphenyl)-1-phenylbenzimidazole;
7-(4-Benzamidyl)-5-cyano-1-phenylbenzimidazole;
7-(3-Acetamidophenyl)-5-hydroxymethyl-1-phenylbenzimidazole;
7-(3-Ethylaminophenyl)-5-hydroxymethyl-1-phenylbenzimidazole;
7-(3-Dimethylaminophenyl)-5-trifluoromethyl-1-phenyl-benzimidazole;
7-(3-Methylaminophenyl)-5-trifluoromethyl-1-phenyl-benzimidazole;
1-Phenyl-7-(3-((4-methylpiperazin-1-yl)methyl)phenyl)-5-trifluoromethylbenzimidazole;
7-(3-(1-Morpholinylmethyl)phenyl)-1-phenyl-5-trifluoromethylbenzimidazole;
7-(3-((Dimethylamino)methyl)phenyl)-1-phenyl-5-trifluoromethylbenzimidazole;
5-Cyano-7-(4-(2-(4-morpholino)ethoxy)phenyl)-1-phenylbenzimidazole;
7-(3-(N-Methyl acetamido)phenyl)-1-phenyl-5-trifluoromethylbenzimidazole;
1-Phenyl-7-(4-pyridyl)-5-trifluoromethylbenzimidazole;
5-(Hydroxymethyl)-1-phenyl-7-(3-trifluoromethoxyphenyl)benzimidazole;
7-(4-pyridyl N-oxide)-1-phenyl-5-trifluoromethylbenzimidazole;
7-(3-chloro-4-pyridyl)-1-phenyl-5-trifluoromethylbenzimidazole;
7-(3-chloro-4-pyridyl-N-oxide)-1-phenyl-5-trifluoromethylbenzimidazole;
7-(3-Acetylphenyl)-1-phenyl-5-trifluoromethylbenzimidazole;
7-(3-Fluorophenyl)-1-phenyl-5-trifluorophenylbenzimidazole;
3-(3-Phenyl-6-trifluoromethyl-3H-benzimidazol-4-yl)acrylic acid methyl ester;
3-(6-Cyano-3-phenyl-3H-benzimidazol-4-yl)acrylic acid methyl ester;
7-(4-Morpholinyl)-1-phenyl-5-trifluoromethylbenzimidazole;
5-t-Butyl-7-(3-dimethylaminophenyl)-1-phenylbenzimidazole;
7-(3-(1-Methoxyethyl)phenyl)-1-phenyl-5-trifluoromethylbenzimidazole;
7-(1-Methyl-5-indolyl)-1-phenyl-5-trifluoromethylbenzimidazole;
7-(3-(1-Hydroxyethyl)phenyl)-1-phenyl-5-trifluoromethylbenzimidazole;
7-(3-Furyl)-1-phenyl-5-trifluoromethylbenzimidazole;
N,N-Diethyl-3-(3-phenyl-6-trifluoromethyl-3H-benzimidazol-4-yl)acrylamide;

1-(4-Methylpiperazin-1-yl)-3-(3-phenyl-6-trifluoromethyl-3H-benzimidazol-4-yl)prop-2-en-1-one;
3-(3-Phenyl-6-trifluoromethyl-3H-benzimidazol-4-yl)-1-piperidinylprop-2-en-1-one;
1-(4-Morpholinyl)-3-(3-phenyl-6-trifluoromethyl-3H-benzimidazol-4-yl)prop-2-en-1-one;
1-(4-Methyl-[1,4]-hexahydrodiazepin-1-yl)-3-(3-phenyl-6-trifluoromethyl-3H-benzimidazol-4-yl)prop-2-en-1-one;
N-(2-Cyanoethyl)-3-(3-phenyl-6-trifluoromethyl-3H-benzimidazol-4-yl)acrylamide;
3-(3-Phenyl-6-trifluoromethyl-3H-benzimidazol-4-yl)-N-propylacrylamide;
N-(2-Dimethylaminoethyl)-3-(3-phenyl-6-trifluoromethyl-3H-benzimidazol-4-yl)acrylamide;
3-(3-Phenyl-6-trifluoromethyl-3H-benzimidazol-4-yl)-1-(4-trifluoromethyl-piperidin-1-yl)prop -2-en-1-one;
7-(3-(2-Hydroxy-2-propyl)phenyl)-1-phenyl-5-trifluoromethylbenzimidazole;
7-(4-Hydroxypiperidinyl)-1-phenyl-5-trifluoromethylbenzimidazole;
7-(3-Fluorophenyl)-5-methyl-1-phenylbenzimidazole;
7-(4-Hydroxybut-1-ynyl)-1-phenyl-5-trifluoromethylbenzimidazole;
7-(1-(1-(4-Hydroxyethylpiperazinyl)ethyl)-1-methylamino)-1-phenyl-5-trifluoromethylbenzimidazole;
7-(1-(1-(4-Methylpiperazinyl)ethyl)-1-methyl)amino-1-phenyl-5-trifluoromethylbenzimidazole;
7-(3-(4-Morpholino)prop-1-ynyl)-1-phenyl-5-trifluoromethylbenzimidazole;
N,N-Diethyl-3-(3-phenyl-6-trifluoromethyl-3H-benzimidazol-4-yl)propionamide;
3-(6-tert-Butyl-3-phenyl-3H-benzimidazol-4-yl)-1-(piperidin-1-yl)prop-2-en-1-one;
N-Ethyl-N-isopropyl-3-(3-phenyl-6-trifluoromethyl-3H-benzimidazol-4-yl)acrylamide;
N-(1-Methylpiperidin-4-yl)methyl-3-(3-phenyl-6-trifluoromethyl-3H-benzimidazol-4-yl) -acrylamide;
N-Methyl-N-(1-methylpyrrolidin-3-yl)-3-(3-phenyl-6-trifluoromethyl-3H-benzimidazol-4-yl)acrylamide;
3-(6-tert-Butyl-3-phenyl-3H-benzimidazol-4-yl)-N-methyl-N-(1-methylpiperidin-4-yl)-acrylamide;
7-(4-(Diethylamino)butyl)-1-phenyl-5-trifluoromethylbenzimidazole; 7-(4-((N-(2-Cyanoethyl)-N-methyl)amino)-1-butyl)-1-phenyl-5-trifluoromethylbenzimidazole;
3-(3-Phenyl-6-trifluoromethyl-3H-benzimidazol-4-yl)-1-(pyrollidin-1-yl)prop-2-en-1-one;
1-(2,5-Dihydropyrrol-1-yl)-3-(3-phenyl-6-trifluoromethyl-3H-benzimidazol-4-yl)prop-2-en-1-one;
N-(2-Cyanoethyl)N-methyl-3-(3-phenyl-6-trifluoromethyl-3H-benzimidazol-4-yl)acrylamide;
1-Phenyl-7-(3-(1-(1,2,3,6-tetrahydropyridinyl))prop-1-ynyl)-5-trifluoromethylbenzimidazole;
1-Phenyl-7-(3-(1-piperidinyl)prop-1-ynyl)-5-trifluoromethylbenzimidazole;
7-[1-(3-Dimethylamino)pyrrolidinyl]-1-phenyl-5-trifluoromethylbenzimidazole;
or an N-oxide thereof, or any of its isomers or any mixture of its isomers, or a pharmaceutically acceptable salt thereof.

8. A pharmaceutical composition, comprising a therapeutically effective amount of a compound of claim 1, or the compound
7-(3-Aminophenyl)-1-phenyl-5-trifluoromethylbenzimidazole,
7-(3-Pyridyl)-1-phenyl-5-trifluoromethylbenzimidazole,
1,7-Diphenyl-5-trifluoromethylbenzimidazole,
7-benzoylamino-1-phenyl-5-trifluoromethylbenzimidazole, or
7-amino-1-phenyl-5-trifluoromethylbenzimidazole,
or an N-oxide thereof, or any of its isomers or any mixture of its isomers, or a pharmaceutically acceptable salt thereof, together with at least one pharmaceutically acceptable carrier, excipient or diluent.

* * * * *